US009676807B2

(12) United States Patent
Zaworotko et al.

(10) Patent No.: US 9,676,807 B2
(45) Date of Patent: Jun. 13, 2017

(54) METAL-ORGANIC MATERIALS (MOMS) FOR ADSORPTION OF POLARIZABLE GASES AND METHODS OF USING MOMS

(71) Applicant: UNIVERSITY OF SOUTH FLORIDA, Tampa, FL (US)

(72) Inventors: Michael Zaworotko, Tampa, FL (US); Mona H. Mohamed, Tampa, FL (US); Sameh Elsaidi, Tampa, FL (US)

(73) Assignee: University of South Florida, Tampa, FL (US)

(*) Notice: Subject to any disclaimer, the term of this patent is extended or adjusted under 35 U.S.C. 154(b) by 5 days.

(21) Appl. No.: 14/437,986

(22) PCT Filed: Oct. 31, 2013

(86) PCT No.: PCT/US2013/067660
§ 371 (c)(1),
(2) Date: Apr. 23, 2015

(87) PCT Pub. No.: WO2014/074378
PCT Pub. Date: May 15, 2014

(65) Prior Publication Data
US 2015/0291641 A1  Oct. 15, 2015

Related U.S. Application Data

(60) Provisional application No. 61/723,931, filed on Nov. 8, 2012, provisional application No. 61/779,692, filed on Mar. 13, 2013.

(51) Int. Cl.
*C07F 11/00* (2006.01)
*C07F 15/06* (2006.01)
*C07F 1/08* (2006.01)
*C07F 3/06* (2006.01)
*B01D 53/02* (2006.01)
(Continued)

(52) U.S. Cl.
CPC ............ *C07F 15/065* (2013.01); *B01D 53/02* (2013.01); *B01J 20/226* (2013.01); *C07F 1/08* (2013.01); *C07F 3/06* (2013.01); *C07F 11/005* (2013.01); *C07F 15/045* (2013.01); *B01D 2253/204* (2013.01); *B01D 2257/504* (2013.01)

(58) Field of Classification Search
CPC .. B01D 53/02; B01D 53/04; B01D 2253/204; B01D 2257/504; B01J 20/226; C07F 11/005; C07F 15/045; C07F 15/065; C07F 1/08; C07F 3/06
USPC ......................... 95/90, 139; 96/108; 502/401
See application file for complete search history.

(56) References Cited

U.S. PATENT DOCUMENTS

2008/0184881 A1* 8/2008 Zhou ...................... B01J 20/226
                                                                    95/43
2013/0139686 A1* 6/2013 Wilmer .................. B01J 20/223
                                                                    95/127

OTHER PUBLICATIONS

Chen, Y. Q. et al., 'A two-fold interpenetrated coordination framework with a rare (3,6)-connected lohl topology: Magnetic properties and photocatalyt-ic behavior' , Crvst. Growth Des.. 2012. vol. 12, pp. 5426-5543 (Sep. 25, 2012).
(Continued)

Primary Examiner — Frank Lawrence
(74) Attorney, Agent, or Firm — Thomas | Horstemeyer, LLP

(57) ABSTRACT

Embodiments of the present disclosure provide for multicomponent metal-organic materials (MOMs), systems including the MOM, systems for separating components in a gas, methods of separating polarizable gases from a gas mixture, and the like.

13 Claims, 24 Drawing Sheets

(51) Int. Cl.
    B01J 20/22      (2006.01)
    C07F 15/04     (2006.01)

(56) References Cited

OTHER PUBLICATIONS

Zou, J. P. et al., 'Two novel metal-organic frameworks (HOFs) with (3,6)-co nnected net topologies: Syntheses, crystal structures, third-order nonlinear optical and luminescent properties', Cryst. Growth Des., 2010, vol. 10, pp. 2613-2619 (Apr. 27, 2010).
Marin, G. et al.. 'Structure diversity in metal-organic frameworks derived from binuclear alkoxo-bridged copper(II) nodes and pyridyl linkers', Cryst. Growth Des., 2008, vol. 8, pp. 964-975 (Feb. 9, 2008).
Zhang, M. D. et al., 'Diverse structures of metal-organic frameworks based on a new star-like tri(4-pyridyl phenyl) amine ligand', Cryst. Growth Des., 2012, vol. 12, pp. 3957-3963 (Jul. 10, 2012).
International Search Report and Written Opinion mailed Feb. 19, 2014.
Moulton, B.; Zaworotko, M. J. Chem. Rev.2001, 101, From Molecules to Crystal Engineering: Supramolecular Isomerism and Polymorphism in Network Solids; 1629-1658.
Batten S. R.; Neville, S. M.; Turner, D. R. Coordination polymers: design, analysis and application; Royal Society of Chemistry: Cambridge, 2009; 438 pages.
Macgillivray, L.R. Metal-Organic Frameworks: Design and Application; John Wiley & Sons: Hoboken, 2010; 353 pages.
Batten, S. R.; Robson, R. Angew. ChemInform Abstract: Interprenetrating Nets;., Int. Ed. 1998, 37, 1460; 36 pages.
Blake, A. J. et al; Inorganic crystal engineering using self-assembly of tailored building blocks; Chem. Rev. 1999, 183, 117; 22 pages.
Li, J.-R. et al; Selective gas adsorption and separation in metal—organic frameworks; Chem. Soc. Rev. 2009, 38, 1477; 29 pages.
Suh, M. P., et al; Hydrogen Storage in MetalOrganic Frameworks Chem. Rev. 2012, 112, 782; 54 pages.
Sumida, K. et al. Chem. Rev. 2012, Carbon Dioxide Capture in MetalOrganic Frameworks; 112, 724; 58 pages.
Lee, J. et al.; Metal—organic framework materials as catalysts; Chem. Soc. Rev. 2009, 38, 1450; 11 pages.
Horcajada, P. et al.; MetalOrganic Frameworks in Biomedicine Chem. Rev.2012, 112, 1232; 37 pages.
McKinlay, A. C. et al; BioMofs: Metal-Organic Frameworks for Biological and Medical Applications; Chem., Int. Ed. 2010, 49, 6260; 8 pages.
Kurmoo, M. Magnetic metal-organic frameworksw; Chem. Soc. Rev. 2009, 38, 1353; 28 pages.
Weng, D.-F. et al.; Molecule-based magnets themed issue; Chem. Soc. Rev. 2011, 40,3157; 27 pages.
Givaja, G. et al; Electrical conductive coordination polymers; Chem. Soc. Rev. 2012, 41, 115; 34 pages.
Zeitler, T. R. et al; Grand Canonical Monte Carlo Simulation of Low-Pressure Methane Adsorption in Nanoporous Framework Materials for Sensing Applications; J. A. J. Phys. Chem. C 2012, 116, 3492; 11 pages.
Banerjee, R. et al; Control of Pore Size and Functionality in Isoreticular Zeolitic Imidazolate Frameworks and their Carbon Dioxide Selective Capture Properties; J. Am. Chem. Soc. 2009, 131, 3875; 3 pages.
Kitagawa, S.; et al; Pore surface engineering of microporous coordination polymers Chem. Commun. 2006, 701; 7 pages.
Kawano, M. et al; The Modular Synthesis of Functional Porous Coordination Networks J. Am. Chem. Soc. 2007, 129, 15418; 2 pages.
Wang, Z.; Cohen, Modulating Metal-Organic Frameworks to Breathe: A Postsynthetic Covalent Modification Approach; S. M. J. Am. Chem. Soc. 2009, 131, 16675; 3 pages.
Desiraju, G. R. Angew. Crystal Engineering: A Holistic View; Chem. Int. Ed. 2007, 46, 8342.

Abrahams, B. F; Hoskins, B. F.; Robson; A New Type of Infinite 3D Polymeric Network Containing 4-Connect4, Peripherally Linked Metalloporphyrin Building Blocks; R. J. Am. Chem. Soc. 1991, 113, 3606; 2 pages.
Kitagawa, S.; Kitaura, R.; Noro; Functional Porous Coordination Polymers; S.-i. Angew. Chem. Int. Ed. 2004, 43, 2334; 42 pages.
Robinson, F.; Zaworotko; Triple Interpenetration in [Ag(4,4'-bipyridine)][N03], a Cationic Polymer with a Three-dimensional Motif Generated by Self-assembly of 'T-shaped' Building Blocks, M. J. J. Chem. Soc.-Chem. Commun 1995, pp. 2413-2414.
Fujita, M. et al; Preparation, Clathration Ability, and Catalysis of a Two-Dimensional Square Network Material Composed of Cadmium (11) and 4,Y-BipyridineJ. Am. Chem. Soc. 1994, 116, 1151-1152.
Subramanian, S.; Zaworotko; Porous Solids by Design: [Zn(4,4'-bpy)2(SiF,)l,*x DMF, a Single Framework Octahedral Coordination Polymer with Large Square Channels; M. J. Angew. Chem., Int. Ed. 1995, 34, 2561; 3 pages.
Lin, M.-J.; Jouaiti, A.; Kyritsakas, N.; Hosseini, M. W. CrystEngComm 2011, 13, 776.
Kopf, A.; Maggard, P.A.; Stern, C.L.;Poeppelmeier, K.R. Acta Cryst. C 2005, C61, m165.
Kopf, A. et a; Poly[nickel(II)-di-f.I-4,4111-bipyridyl-K4N:N111-f.I-dichromato-K20:0111] and poly[copper(II)-di-f.I-4,4'-bipyridyl-K4N:N111-f.I-dichromato-K20:0111];. Acta Cryst. C 2005, C61, m165; 4 pages.
Noro, Shin-ichiro. et al; Framework Engineering by Anions and Porous Functionalities of Cu(II)/4,4'-bpy Coordination Polymers; J. Am. Chem. Soc. 2002, 124, 2568. 16 pages.
Lin, M. J. et al; Molecular tectonics: modulation of size and shape of cuboid 3-D coordination networks, M. W. CrystEngComm 2009, 11, 189-191; 3 pages.
Uemura, K.; Maeda, A.; Maji, T. K.; Kanoo, P.; Kita, H. Eur. J. Inorg. Chem. 2009, 2329.
Chen, B.; Ockwig, N. W.; Millward, A. R.; Contreras, D. S.; Yaghi, O. M. Angew. Chem., Int. Ed. 2005, 44, 4745.
Wang, X.-S.; Ma, S.; Forster, P. M.; Yuan, D.; Eckert, J.; Lóopez, J. J.; Murphy, B. J.; Parise, J. B.; Zhou, H.-C. Angew. Chem., Int. Ed. 2008, 47, 7263.
Britt, D.; Furukawa, H.; Wang, B.; Glover, T. G.; Yaghi, O. M. Proc. Natl. Acad. Sci. 2009, 106, 20637.
Lin, J.-B.; Zhang, J.-P.; Chen, X.-M. J. Am. Chem. Soc. 2010,132, 6654.
Lin, Q.; Wu, T.; Zheng, S.-T.; Bu, X.; Feng, P. J. Am. Chem. Soc. 2012, 134, 784.
Demessence, A.; D'Alessandro, D. M.; Foo, M. L.; Long, J. R. J. Am. Chem. Soc. 2009, 131, 8784.
Vaidhyanathan, R.; Iremonger, S.S.; Shimizu, G.K.H.; Boyd, P.; Alavi, S.; Woo, T.K. Science, 2010, 330, 650.
Zheng, B.; Bai, J.; Duan, J.; Wojtas, L.; Zaworotko, M. J. J. Am. Chem. Soc. 2010, 133, 748.
Maji, T. K.; Matsuda, R.; Kitagawa, S. Nat. Mater. 2007, 6, 142.
Laskoski, M. C.; LaDuca Jr, R. L.; Rarig Jr, R. S.; Zubieta, J. J. Chem. Soc., Dalton Trans. 1999, 3467.
LaDuca Jr, R. L.; Desiak, M.; Rarig Jr, R. S.; Zubieta, J. Inorganica Chimica Acta 2002, 332, 79.
Gong, Y.; Liu, T.; Tang, W.; Wu, F.; Gao, W.; Hu, C. J. Solid State Chem. 2007, 180, 1476.
Blatov, V. A. IUCr CompComm Newsletter 2006, 7, 4;. http://www.topos.samsu.ru.
O'Keeffe, M.; Peskov, M.A.; Ramsden, S. J.; Yaghi, O. M.Acc. Chem. Res. 2008, 41, 1782.
O'Keeffe, M.; Yaghi, O. M. Chem. Rev. 2012, 112, 675.
Carlucci, L.; Ciani, G.; Proserpio, D. M. Coord. Chem. Rev. 2003, 246, 247.
Zheng, S.-T.; Wu, T.; Chou, C.; Fuhr, A.; Feng, P.; Bu, X. J. Am. Chem. Soc. 2012, 134, 4517.
Zheng, S.-T.; Mao, C.; Wu, T.; Lee, S.; Feng, P.; Bu, X. J. Am. Chem. Soc. 2012, 134, 11936.
Noro, S.; Kitagawa, S.; Kondo, M.; Seki, K. Angew. Chem., Int. Ed. 2000, 39, 2082.

(56) References Cited

OTHER PUBLICATIONS

Laskoski, et al., Oxoanion influences on the self-assembly of cationic co-ordination complex polymers of the nickel (II)-di-4-pyridylamine family, Jan. 1, 1999, No. 19, pp. 3467-3472.

Laduca, et al., A bimetallic oxide hybrid material constructed from a coordination complex polymer and molybdenum oxide subinits, Inorganica Chimica Acta, Jan. 1, 2002.

Wang, et al., An open-framework cobalt molydate possessing {Mo2 o7} building block: hydrothermal synthesis and structural characterization of [CoMo2O7(4,4'-bipy)1.5], Journal of Coordination Chemistry, vol. 60, No. 23, Dec. 1, 2007.

Gong, et al., Anion-directed assembly: Framework conversion in dimensionality and photoluminescence, Journal of Solid State Chemistry, Orlando, FL, vol. 180, No. 4, Apr. 26, 2007.

Foreign search report for EP13853837, dated Apr. 29, 2016.

Burd, S. D.; Ma, S.; Perman, J. A.; Sikora, B. J.; Snurr, R. Q.; Thallapally, P. K.; Tian, J.; Wojtas, L.; Zaworotko, M. J. J. Am. Chem. Soc.2012, 134, 3663.

Noro, S.-i.; Tanaka, D.; Sakamoto, H.; Shimomura, S.; Kitagawa, S.; Takeda, S.; Uemura, K.; Kita, H.; Akutagawa, T.; Nakamura, T. Chem. Mat. 2009, 21, 3346.

Cavenati, S.; Grande, C. A.; Rodrigues, A. E. Ind. Eng. Chem. Res. 2008, 47, 6333.

Bourrelly, S.; Llewellyn, P. L.; Serre, C.; Millange, F.; Loiseau, T.; Férey, G. J. Am. Chem. Soc. 2005, 127, 13519.

Caskey, S. R.; Wong-Foy, A. G.; Matzger, A. J. J. Am. Chem. Soc. 2008, 130, 10870.

Harlick, P. J. E.; Tezel, F. H. Micro. Meso. Mater. 2004, 76, 71.

Vaidhyanathan, R.; Iremonger, S. S.; Dawson, K. W.; Shimizu, G. K. H. Chem. Commun. 2009, 5230.

An, J.; Geib, S. J.; Rosi, N. L. J. Am. Chem. Soc. 2009, 132, 38.

Iremonger, S.S.; Liang, J.; Vaidhyanathan,R.; Martens, I.; Shimizu, G.K.H.; Daff, T.D.; Aghaji, M.Z.; Yeganegi, S.; Woo, T.K. J. Am. Chem. Soc. 2011, 133, 20048.

Mason, J. A.; Sumida, K.; Herm, Z. R.; Krishna, R.; Long, J. R. Energy Environ. Sci. 2011, 4, 3030.

Belof, J. L.; Stern, A. C.; Eddaoudi, M.; Space, B. J. Am. Chem. Soc. 2007, 129, 15202.

Forrest, K. A.; Pham, T.; McLaughlin, K.; Belof, J. L.; Stern, A. C.; Zaworotko, M. J.; Space, B. J. Phys. Chem. C. 2012, 116, 15538.

* cited by examiner

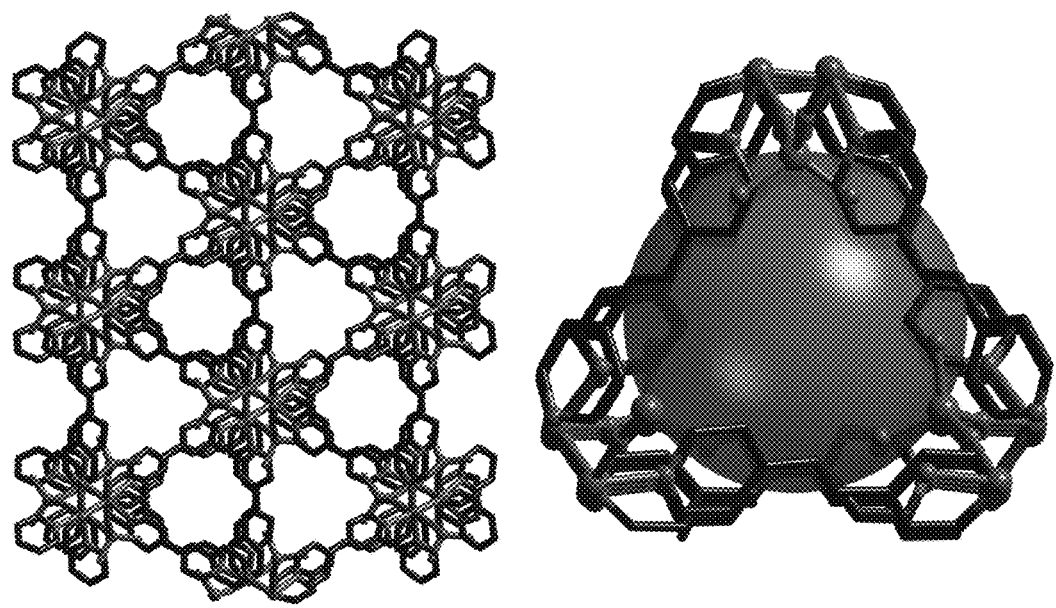
FIG. 1.1
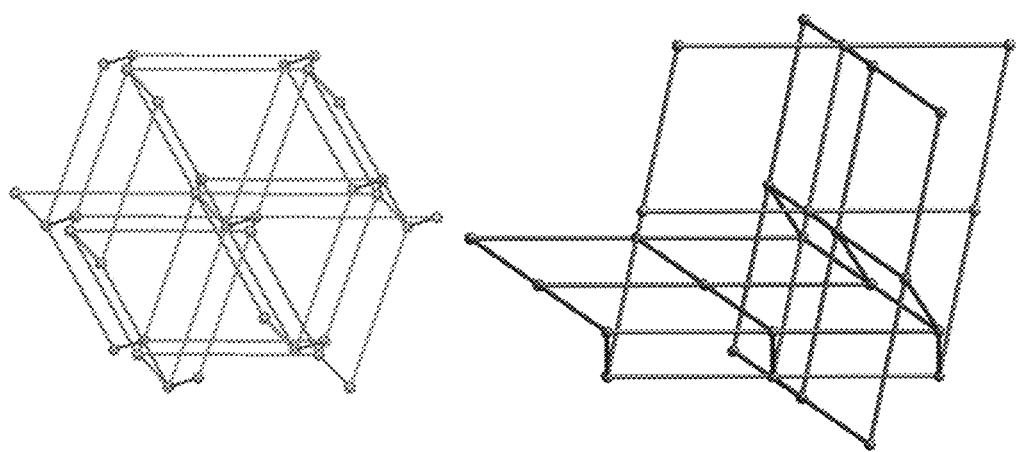
FIG. 1.2A          FIG. 1.2B

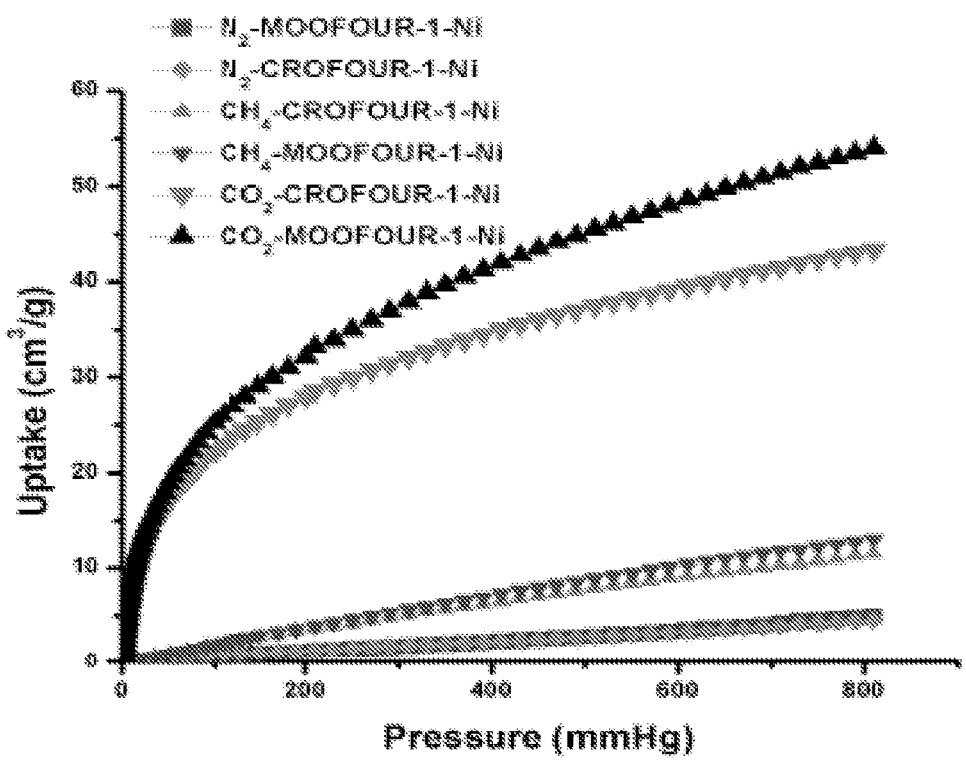
FIG. 1.3
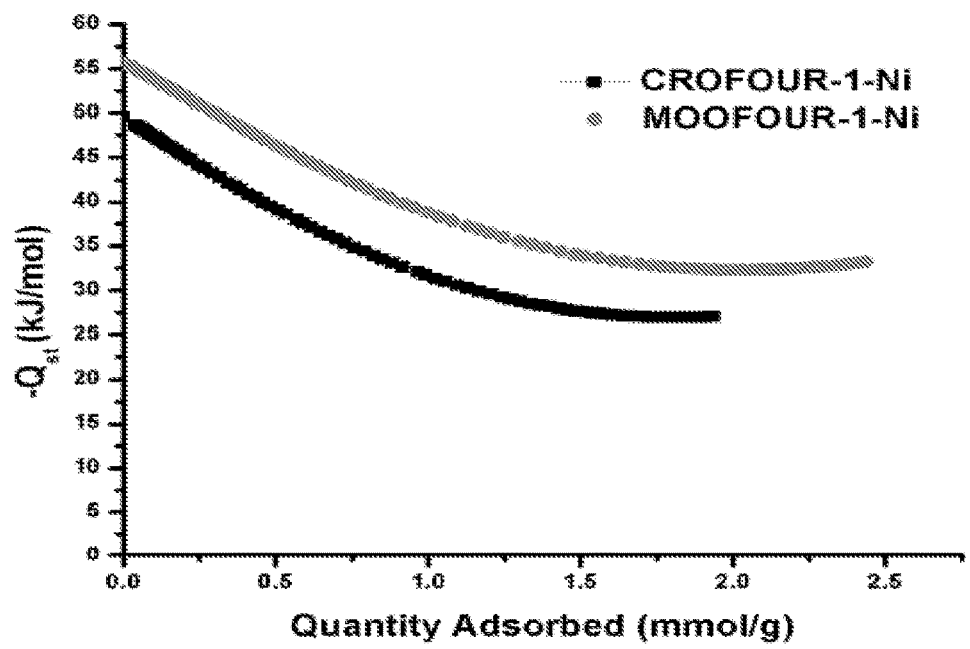
FIG. 1.4

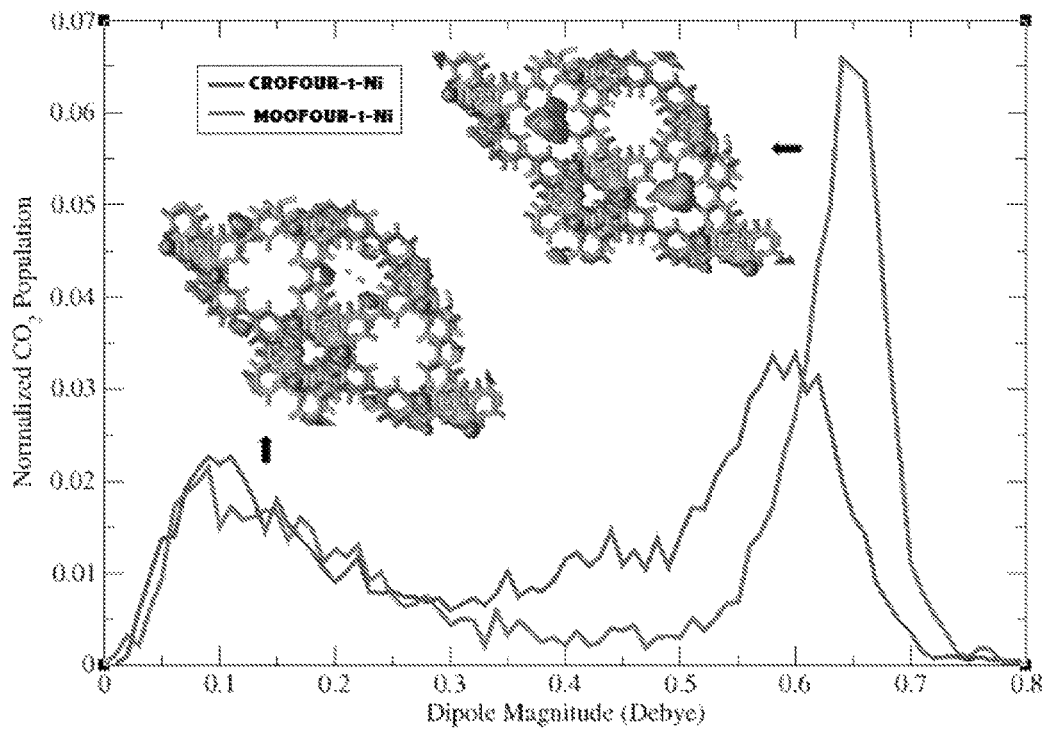
FIG. 1.5
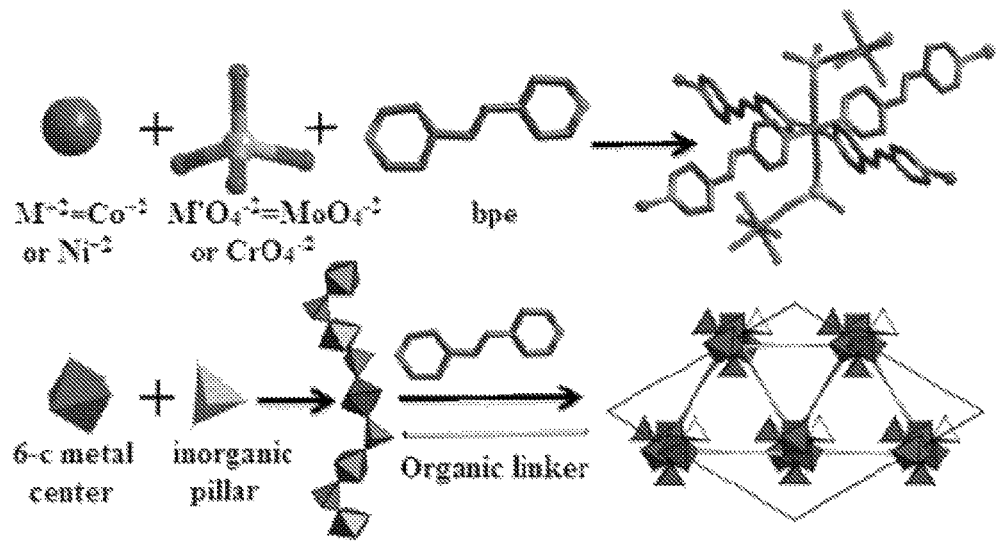
Scheme 1
FIG. 1.6

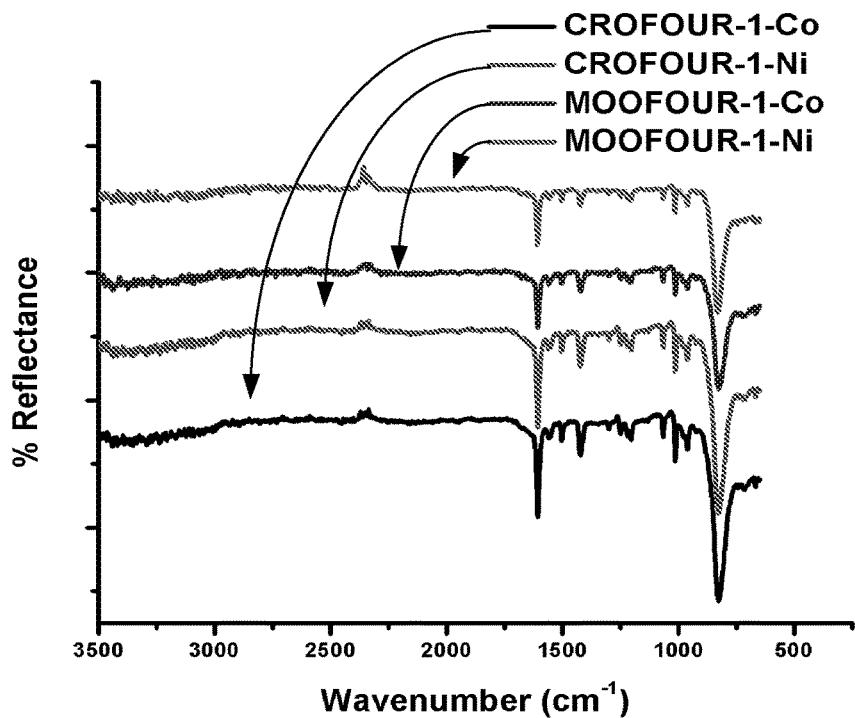
FIG. 1.7
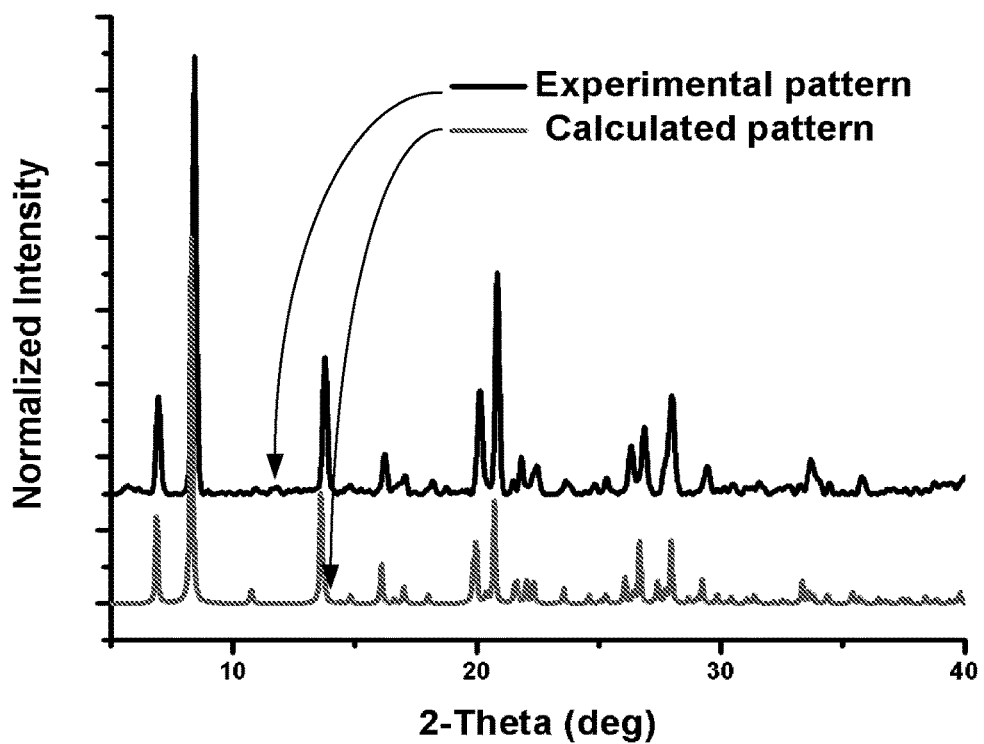
FIG. 1.8

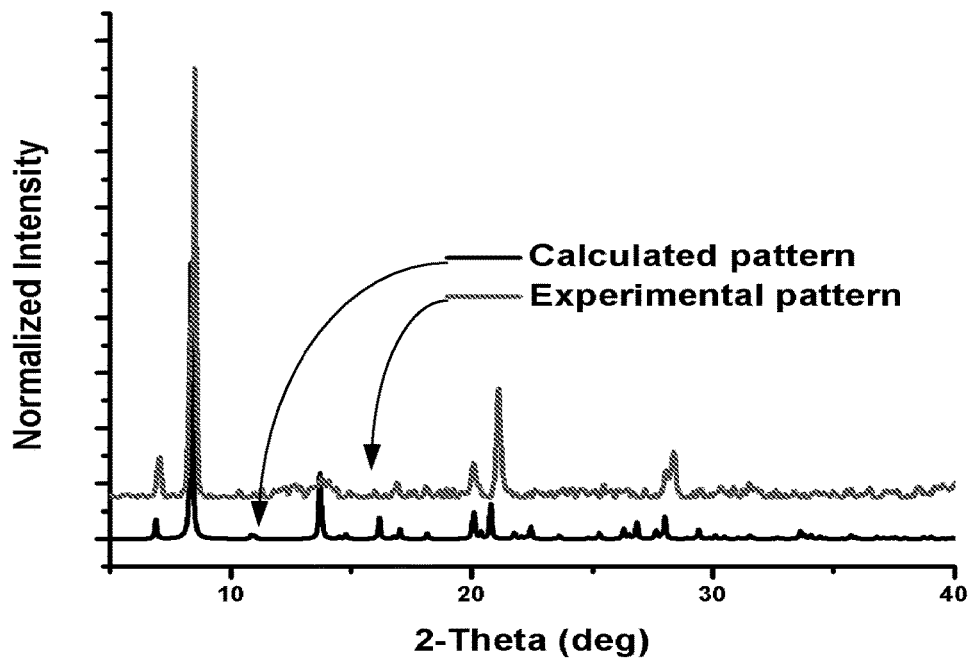
FIG. 1.9
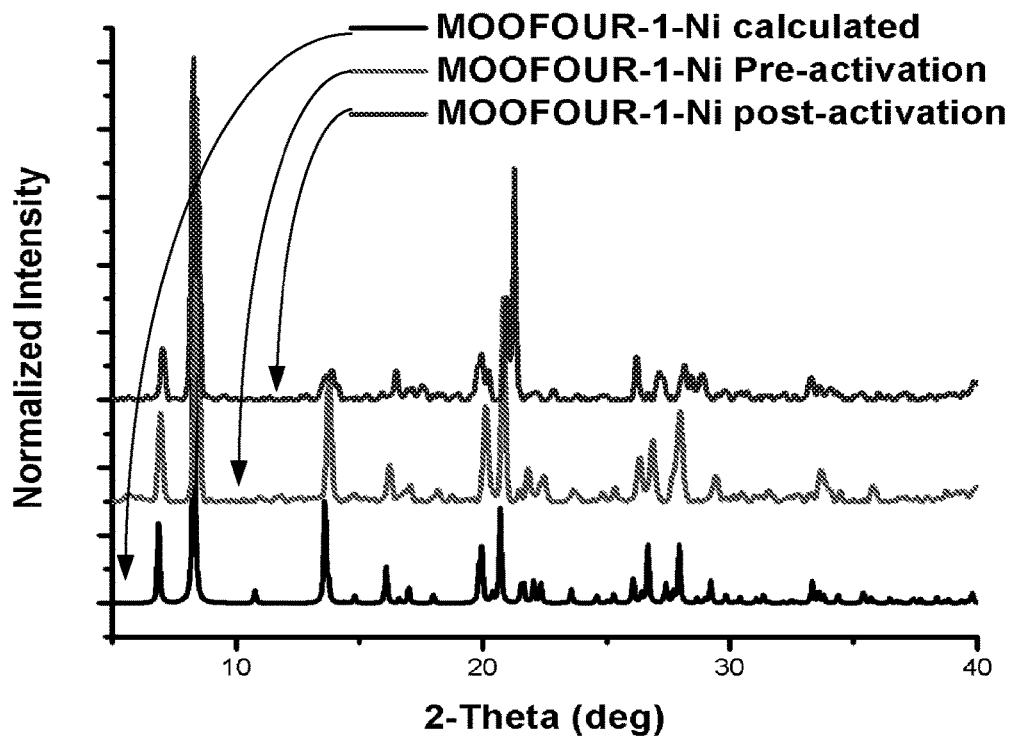
FIG. 1.10

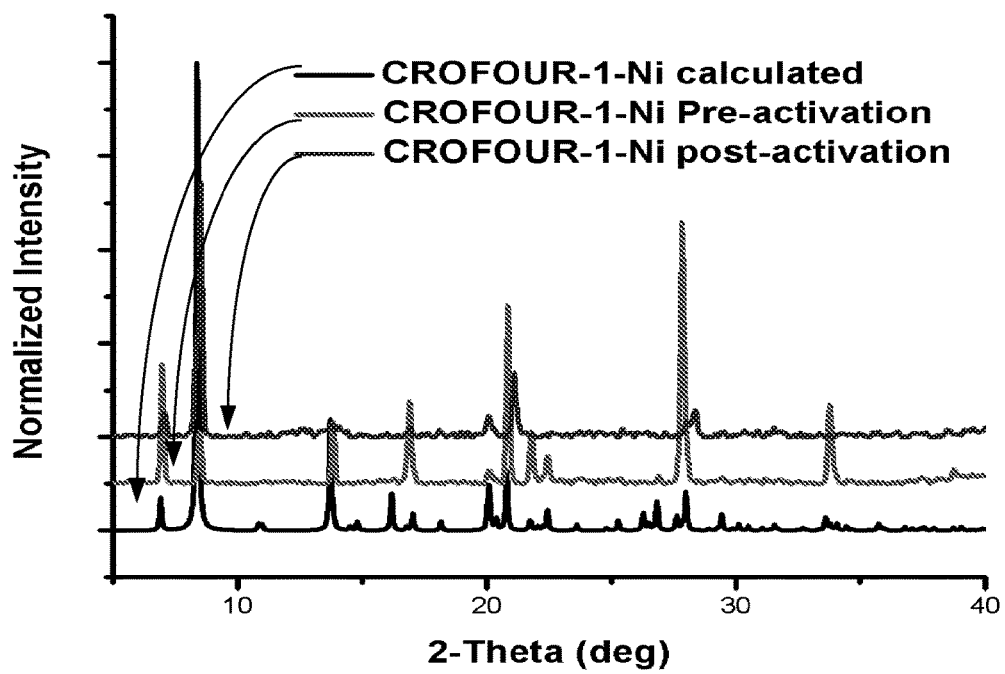
FIG. 1.11
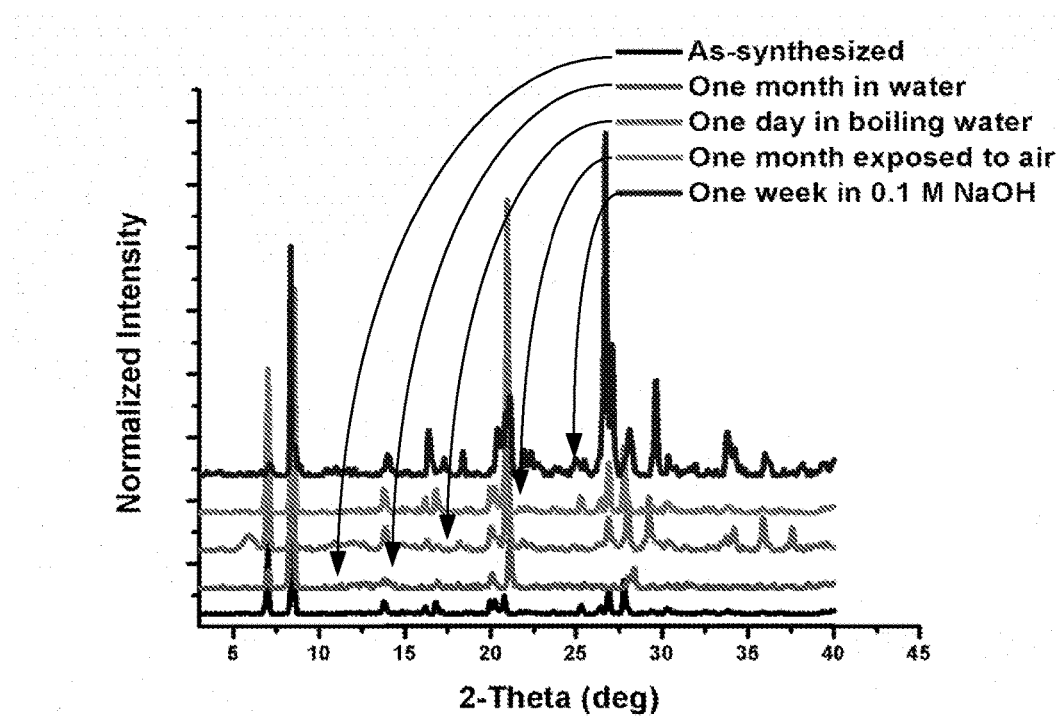
FIG. 1.12

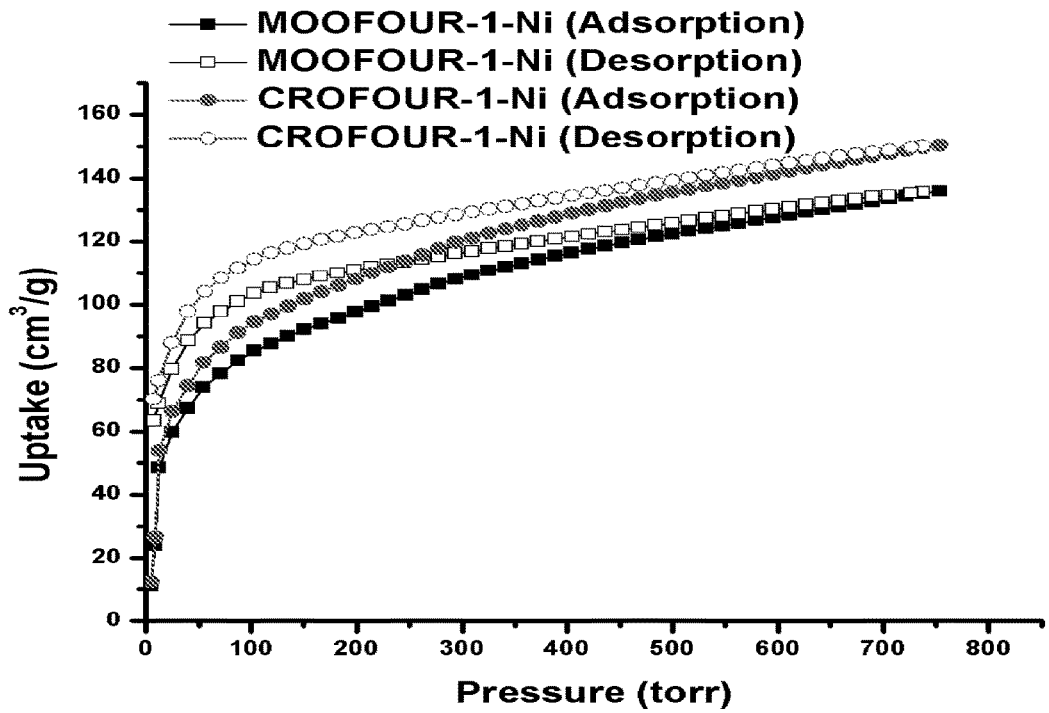
FIG. 1.13
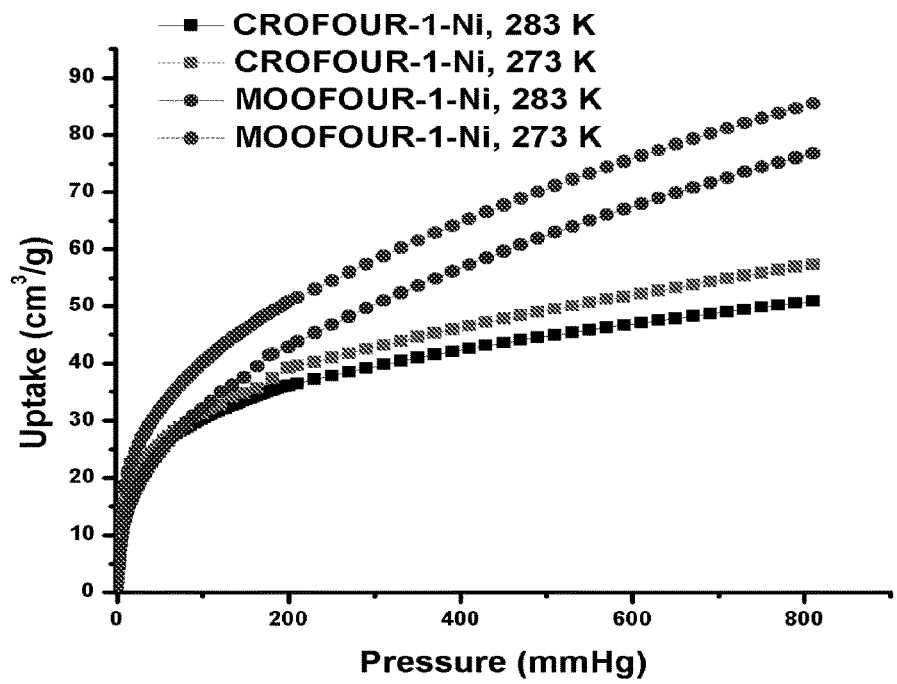
FIG. 1.14

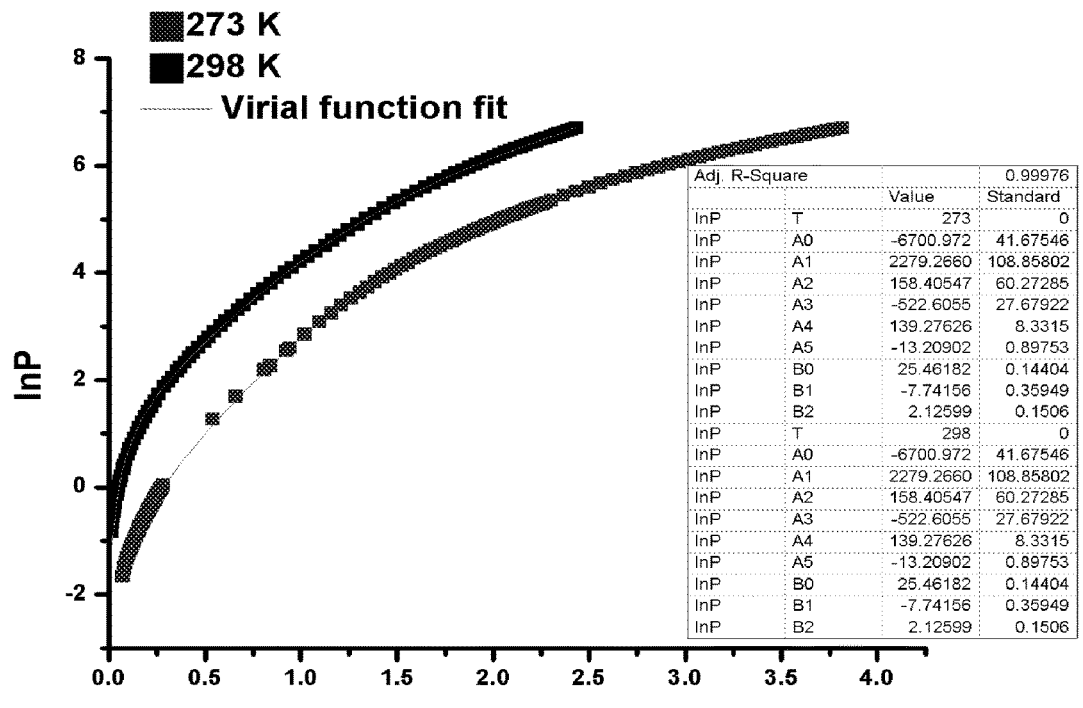
FIG. 1.15
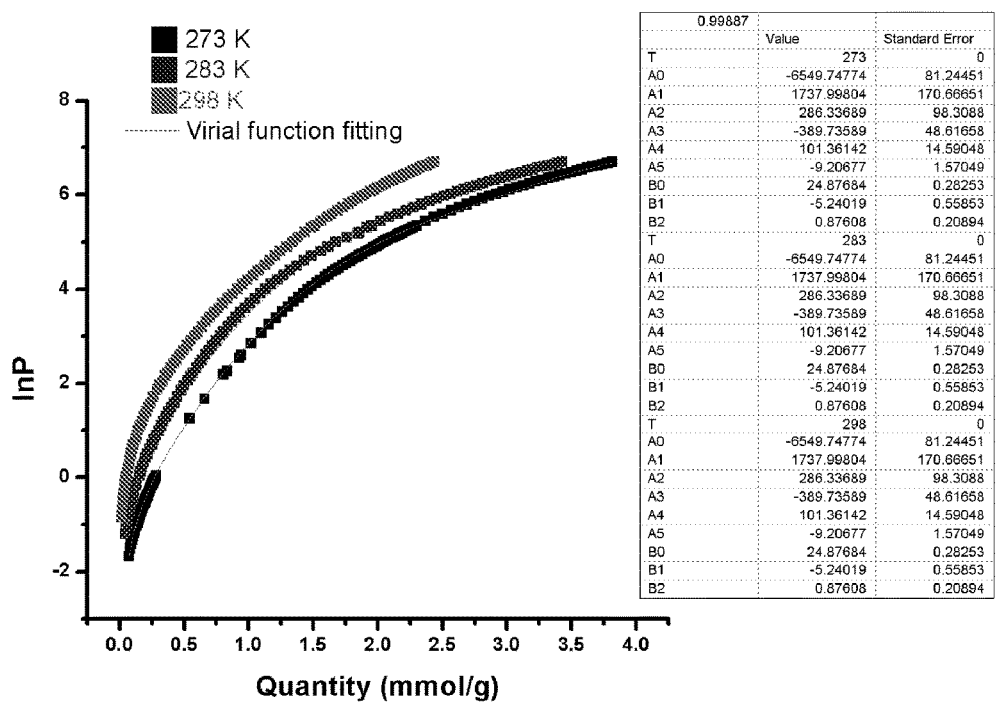
FIG. 1.16

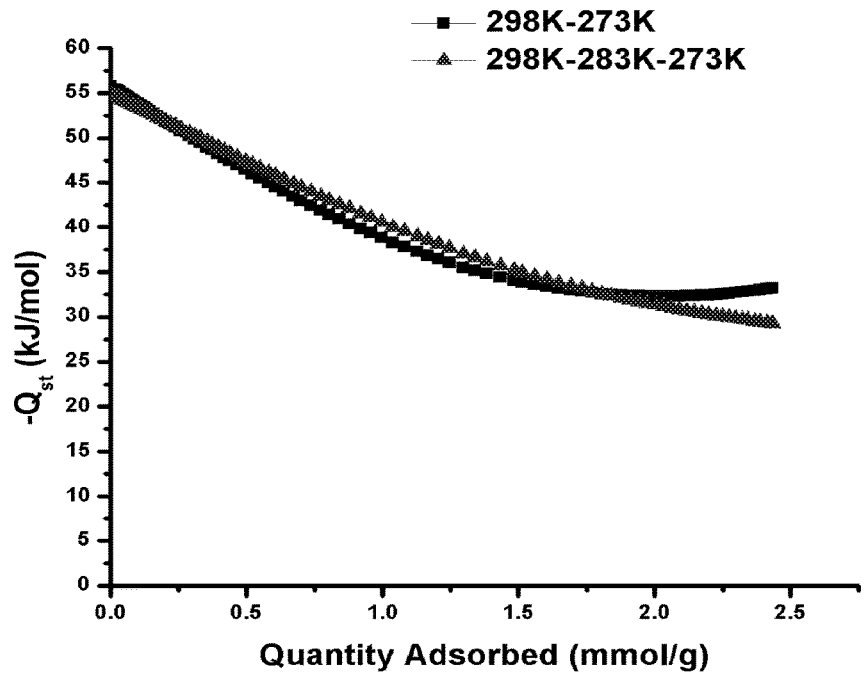
FIG. 1.17
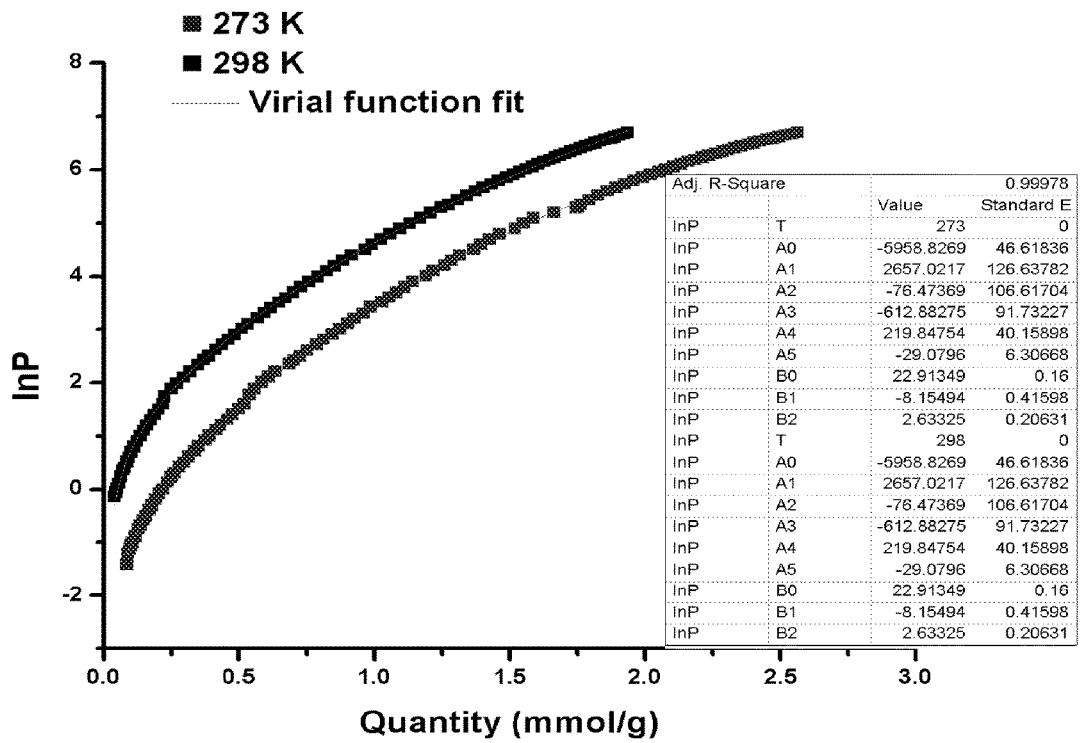
FIG. 1.18

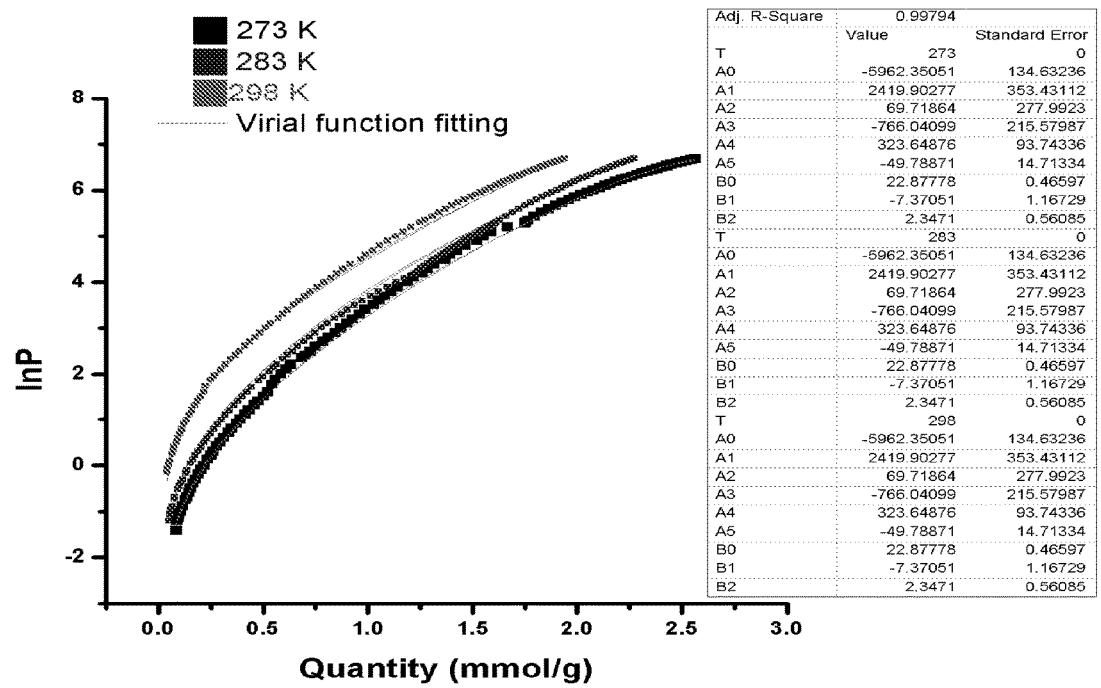
FIG. 1.19
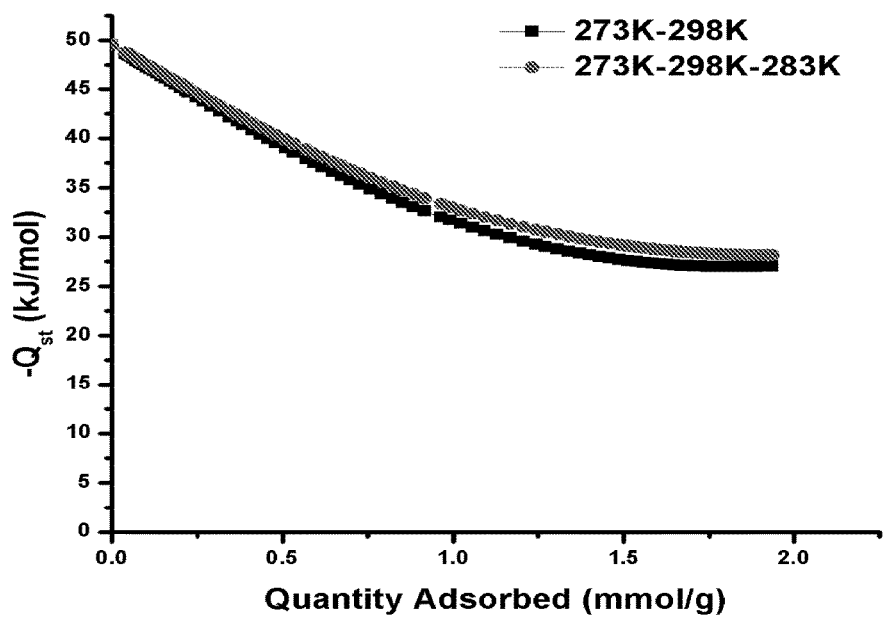
FIG. 1.20

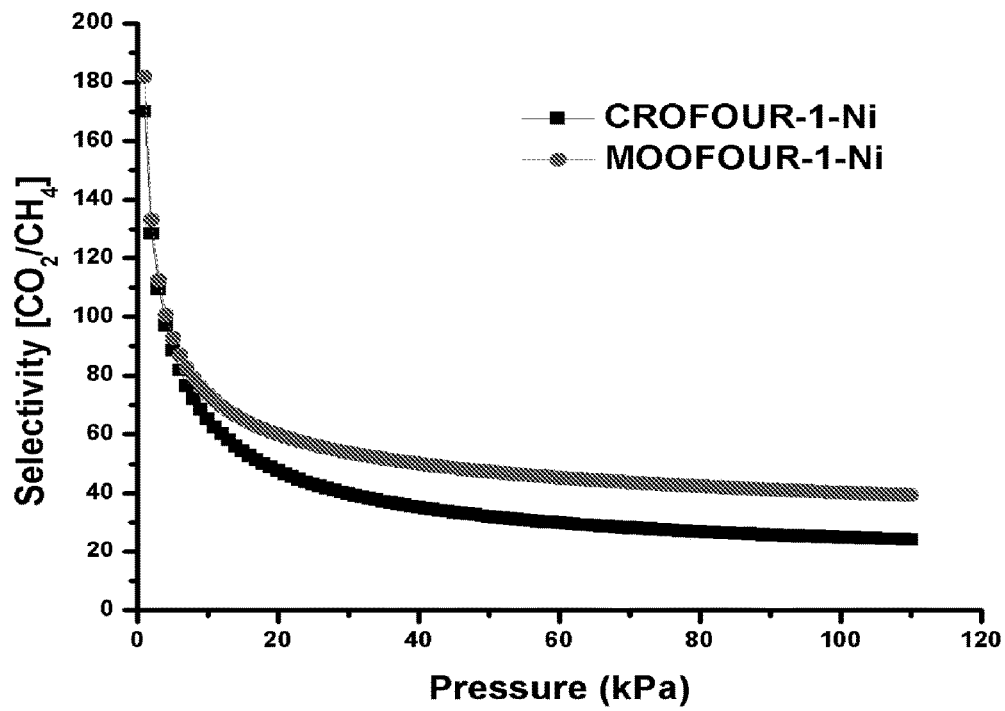
FIG. 1.21
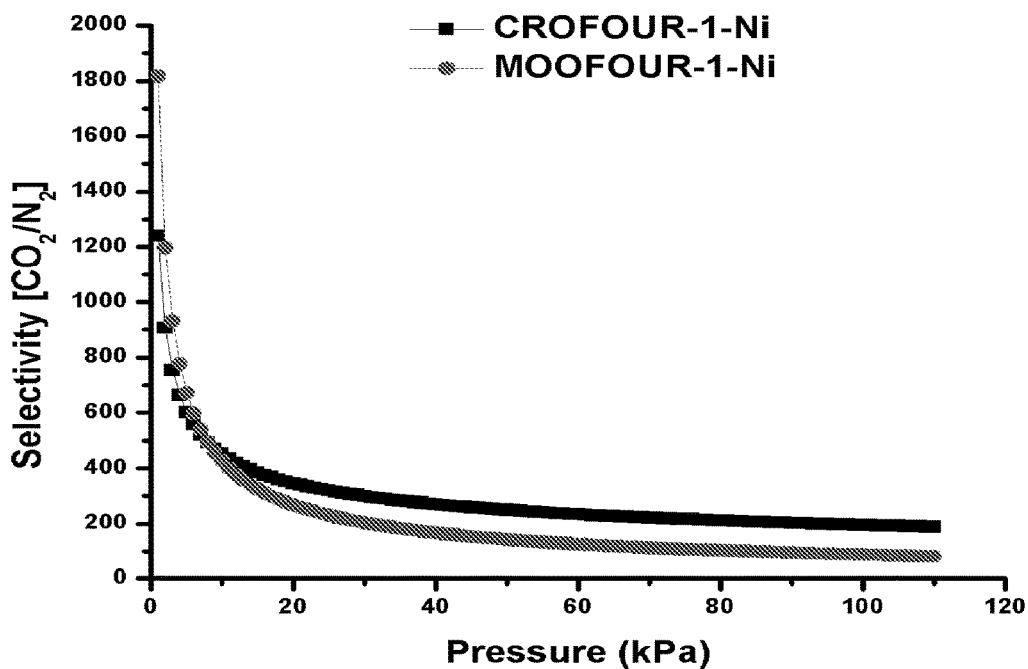
FIG. 1.22

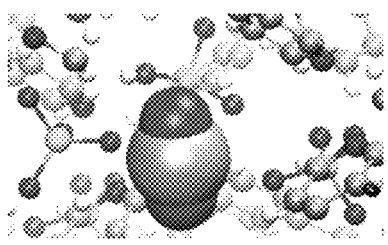
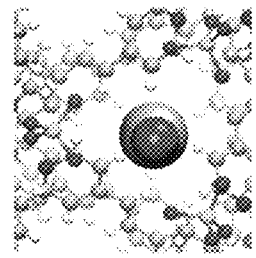
FIG. 1.23A     FIG. 1.23B
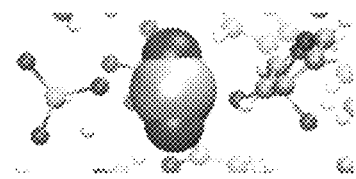
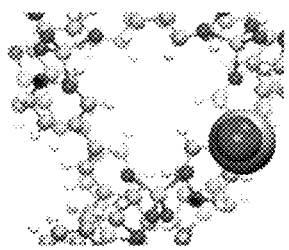
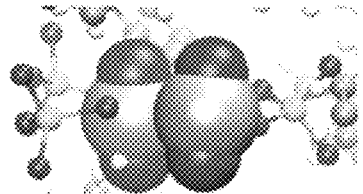
FIG. 1.23C     FIG. 1.23D     FIG. 1.23E
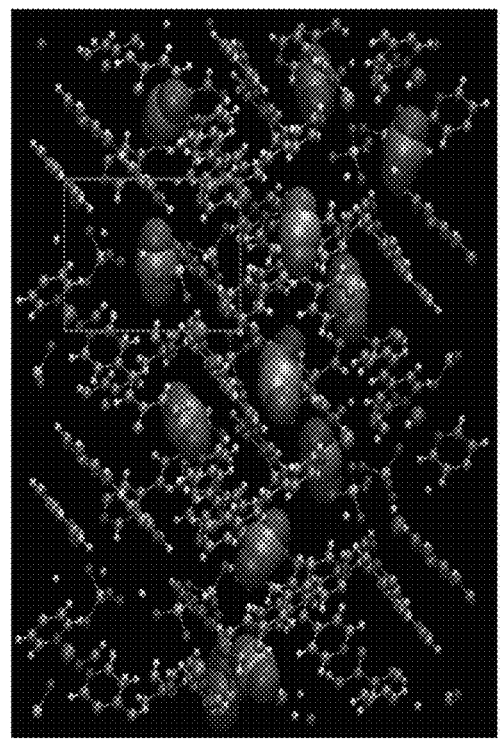
FIG. 1.24

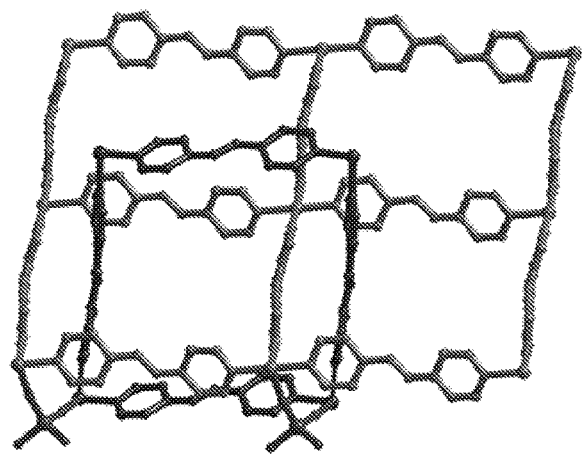
FIG. 2.1
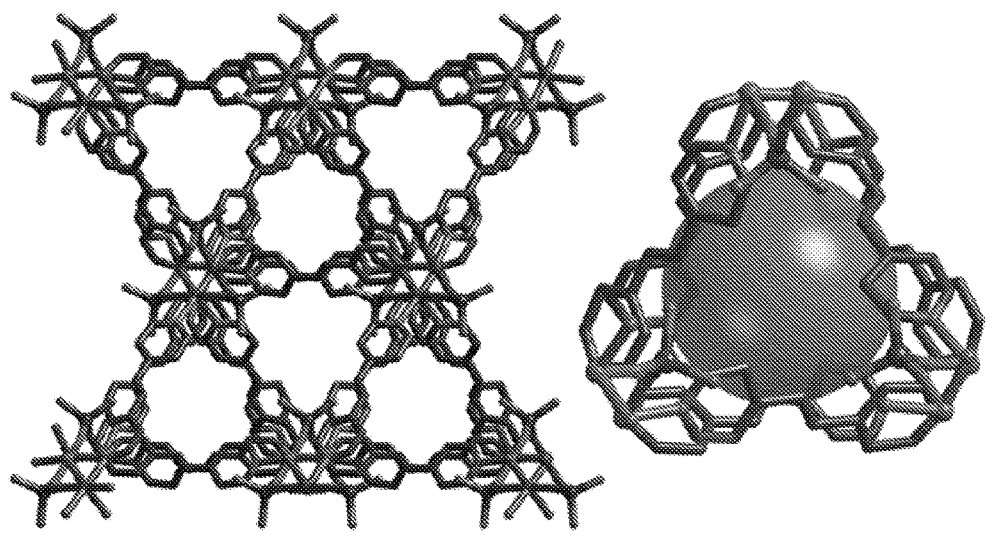
FIG. 2.2

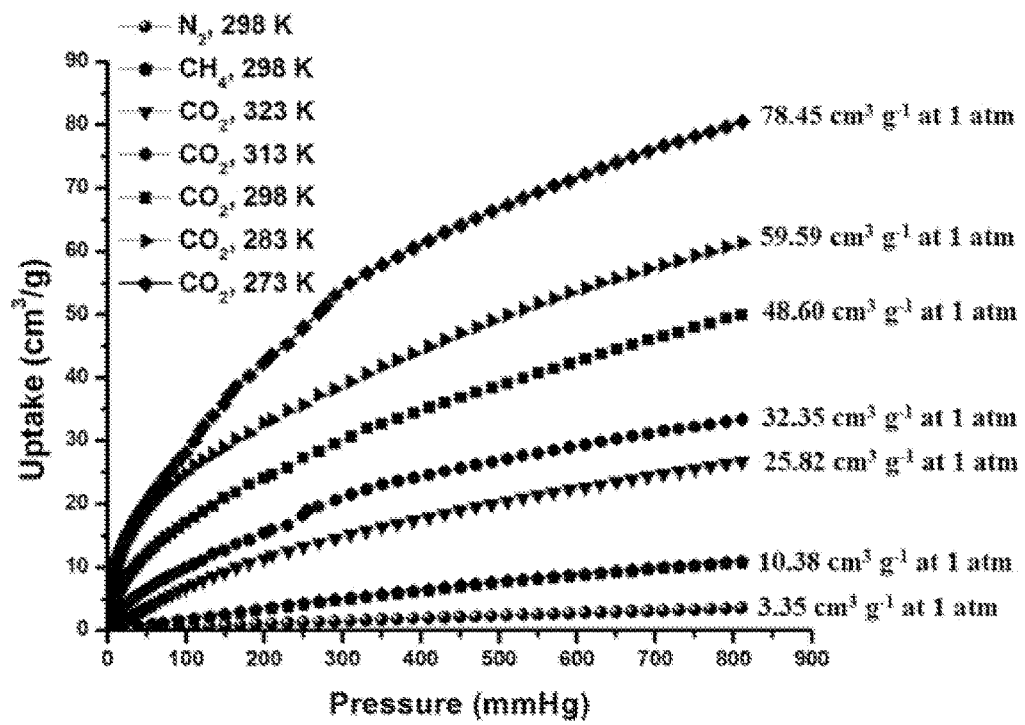
FIG. 2.3
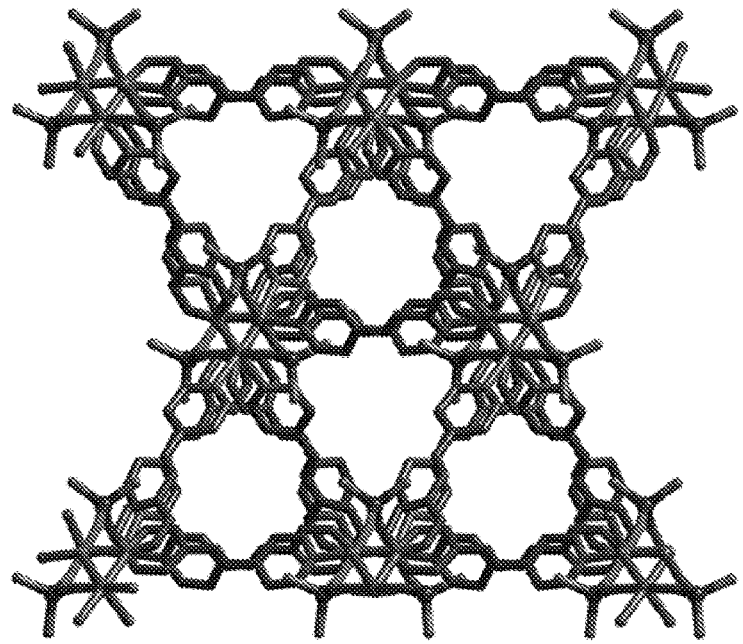
FIG. 3.1

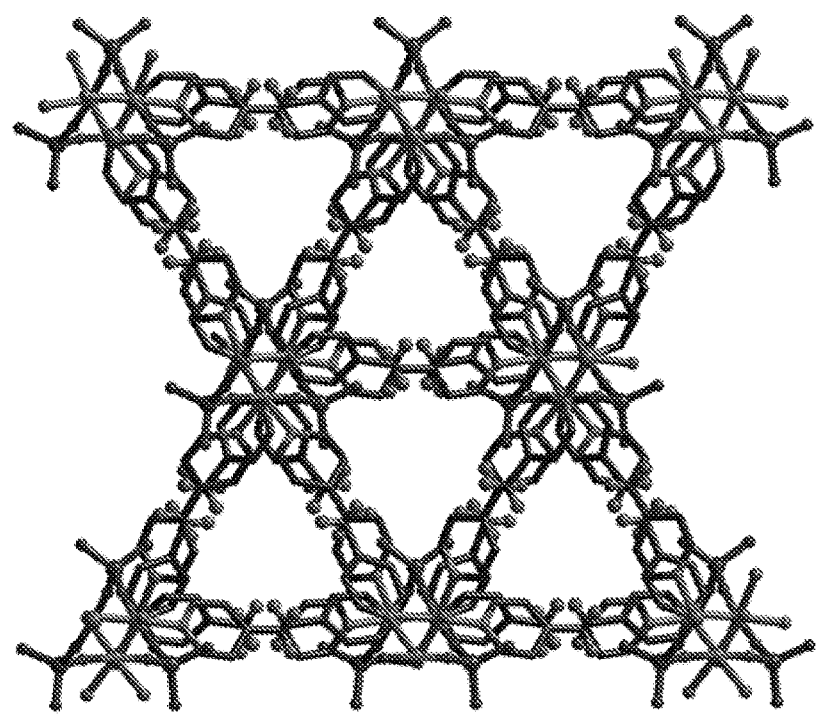
FIG. 4.1
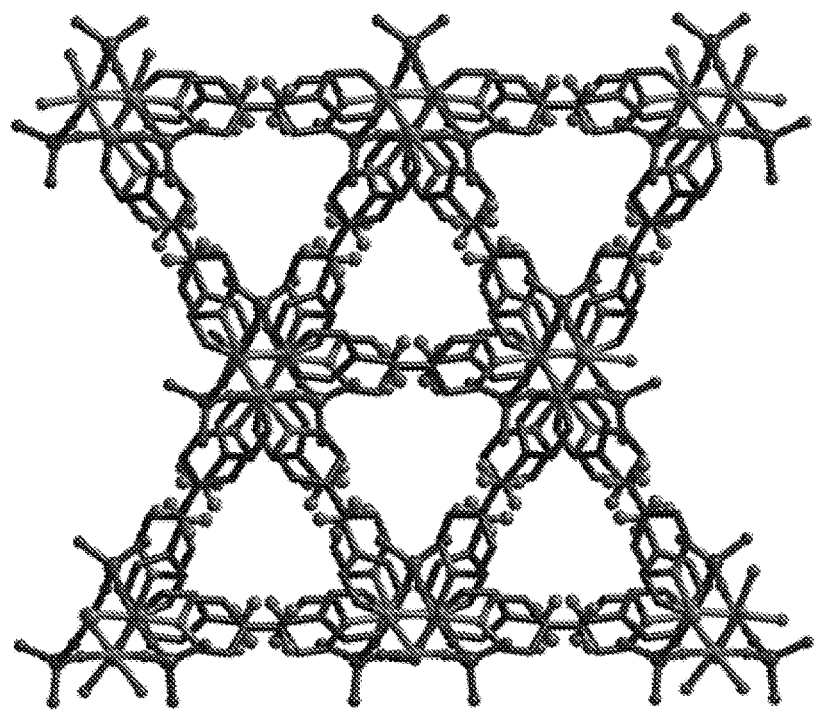
FIG. 5.1

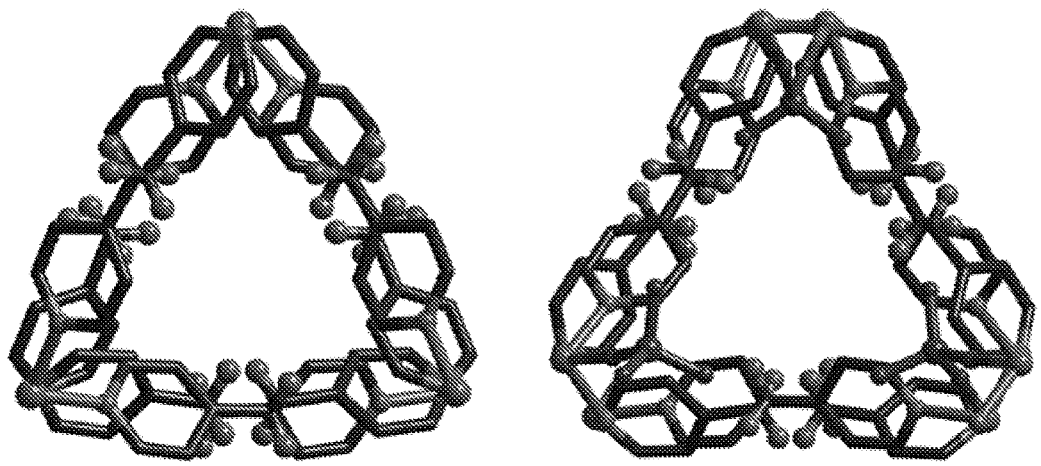
FIG. 5.2
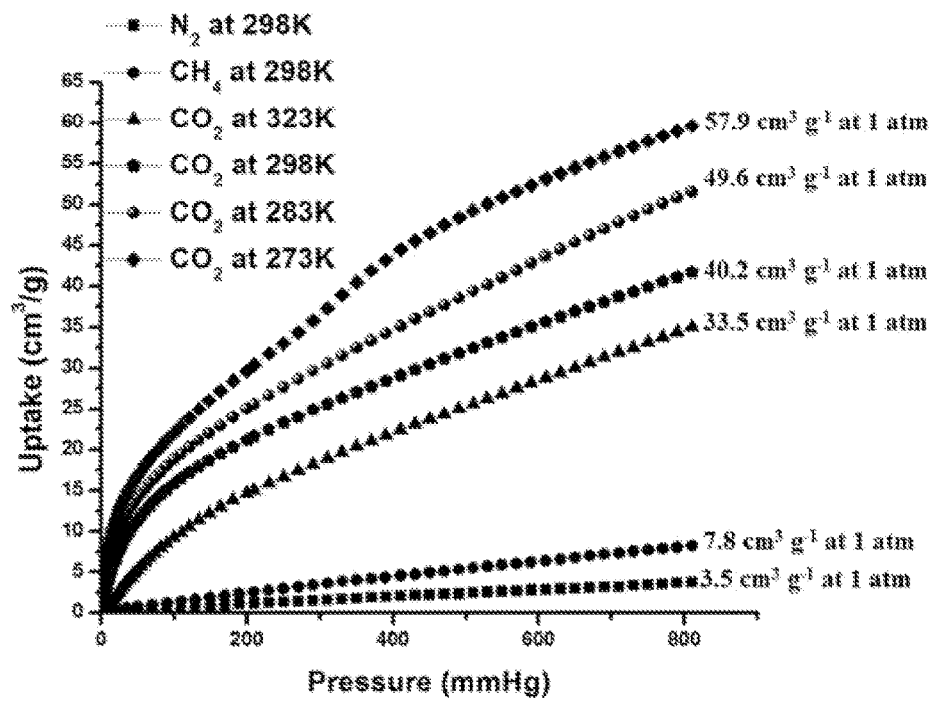
FIG. 5.3

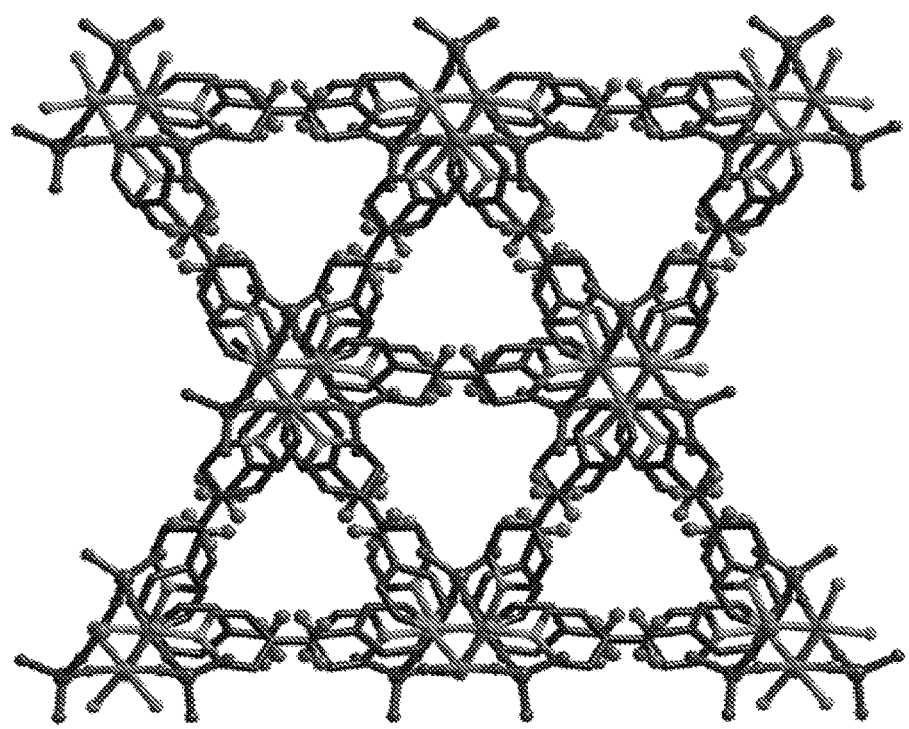
FIG. 6.1
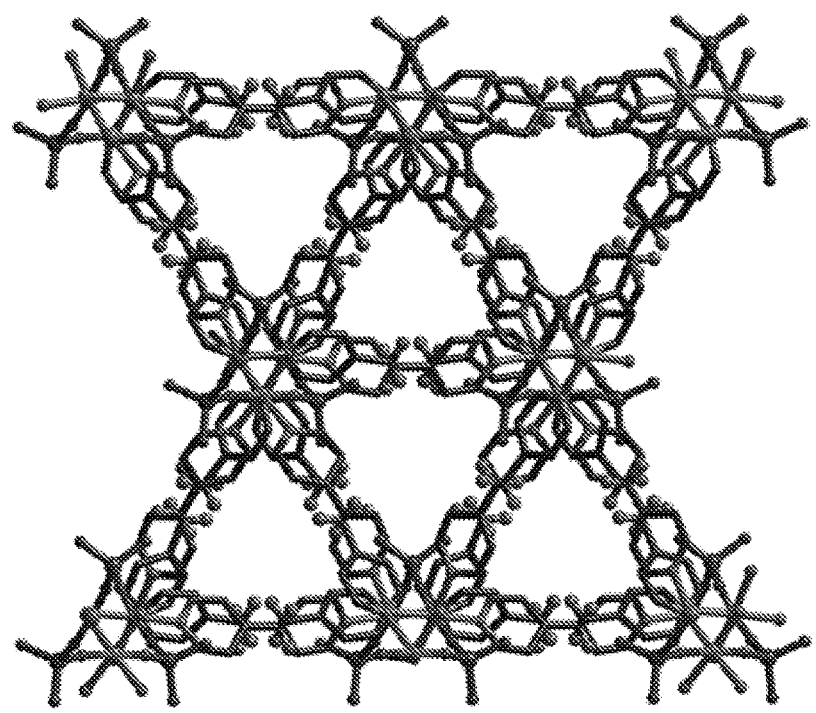
FIG. 7.1

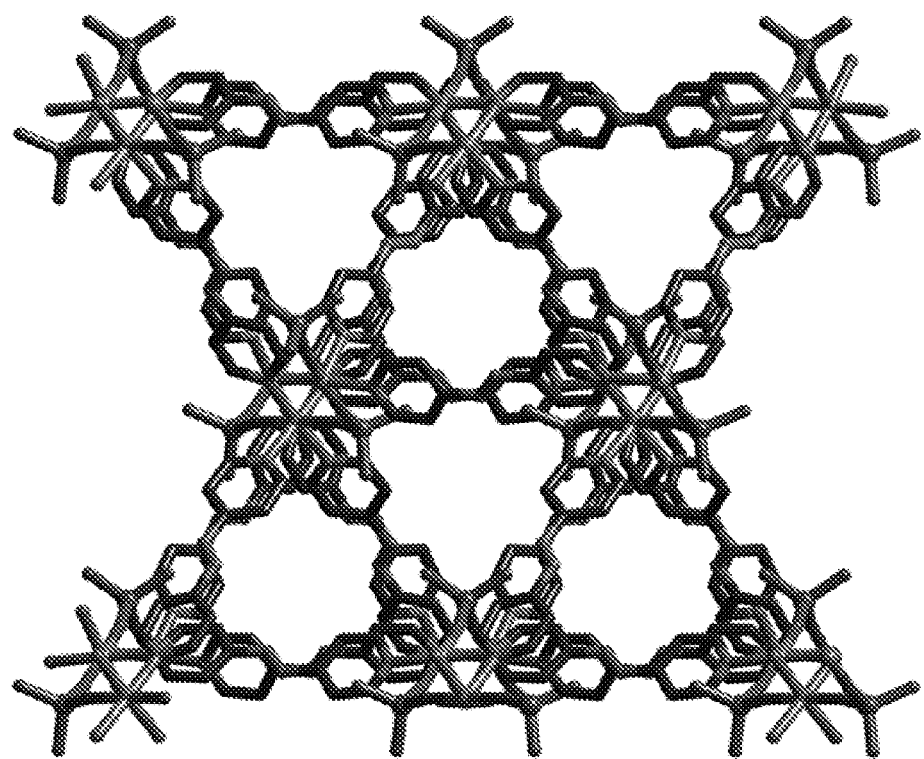
FIG. 8.1
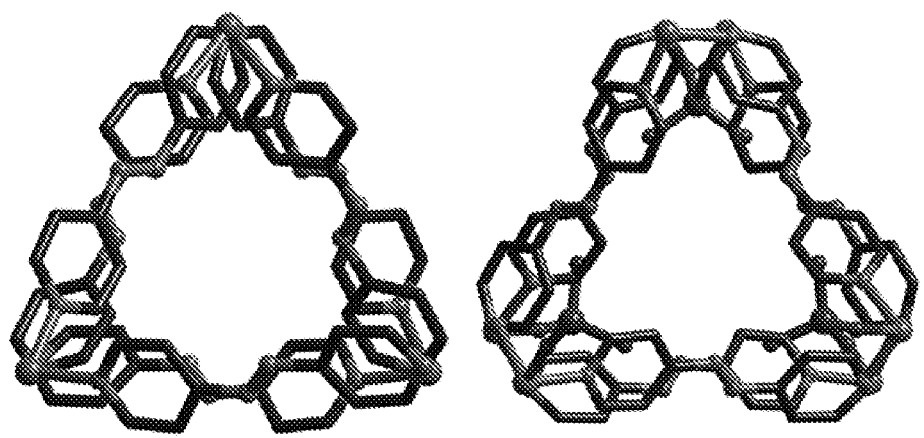
FIG. 8.2

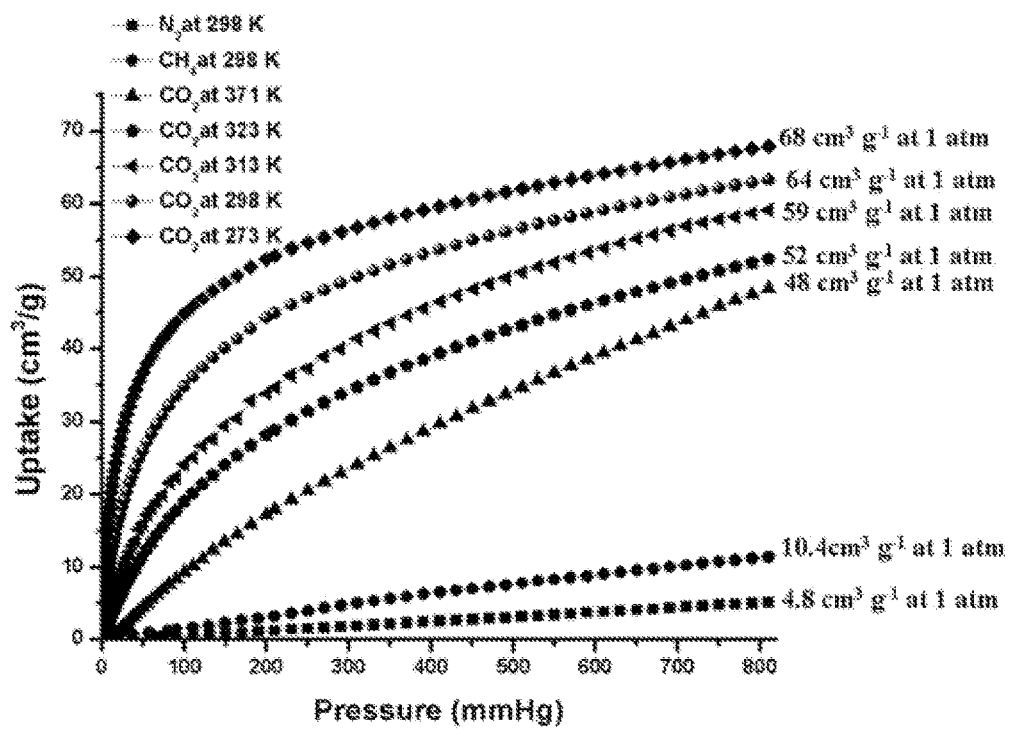
FIG. 8.3
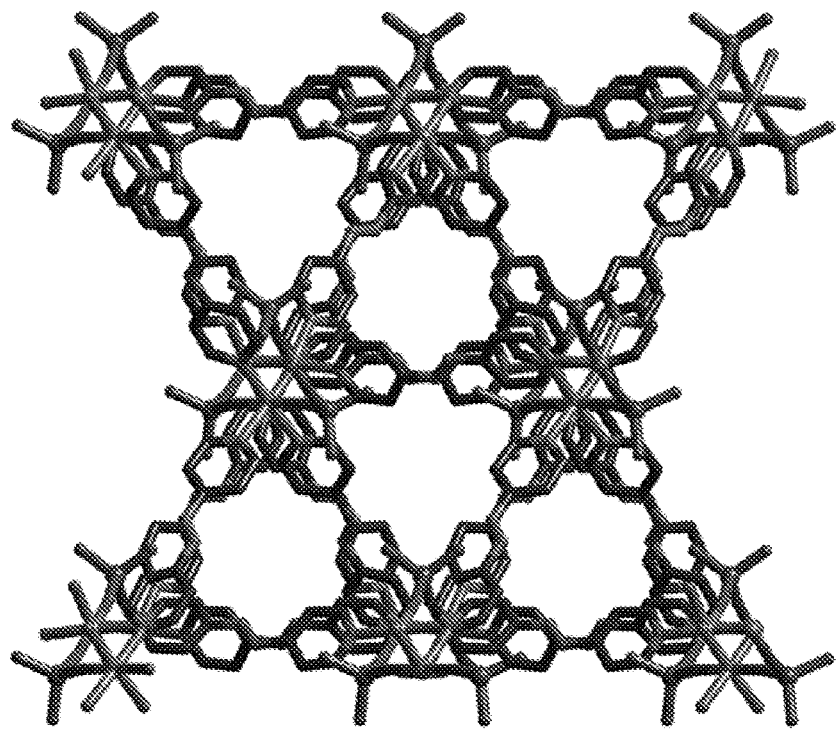
FIG. 9.1

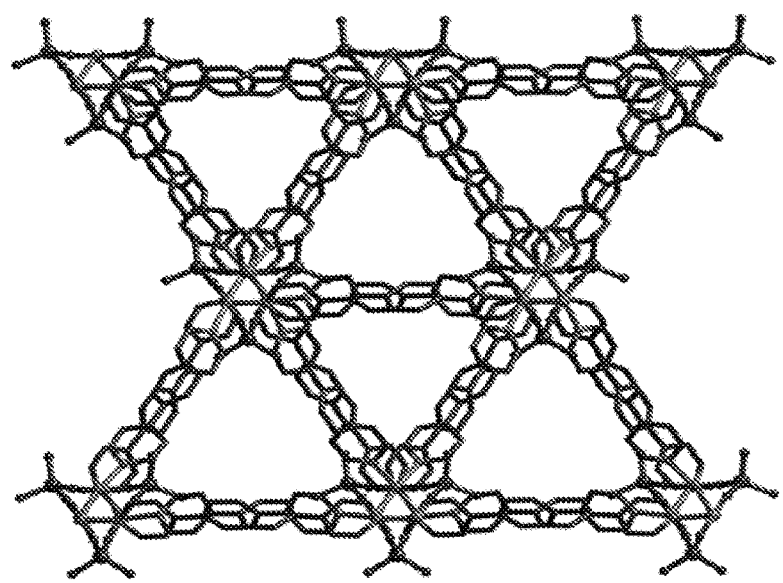
FIG. 10.1
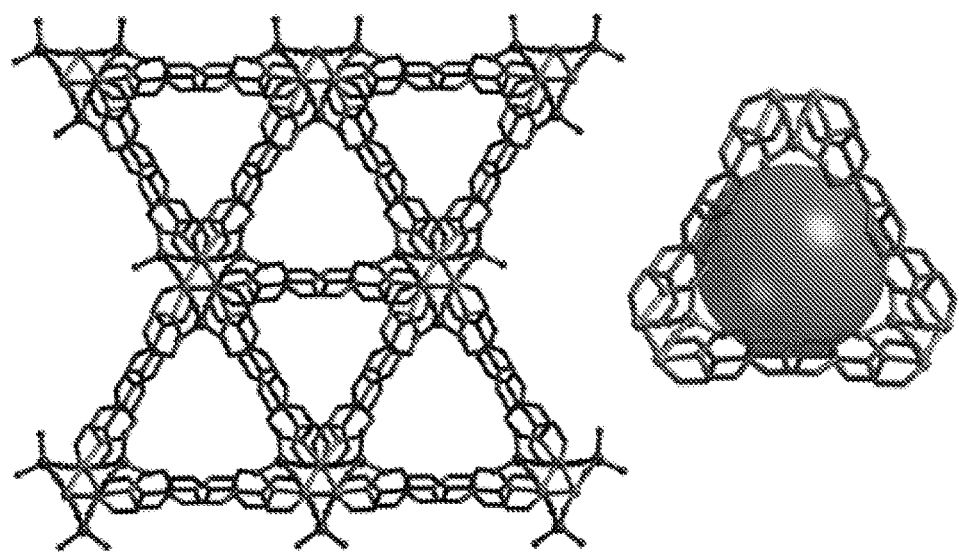
FIG. 11.1

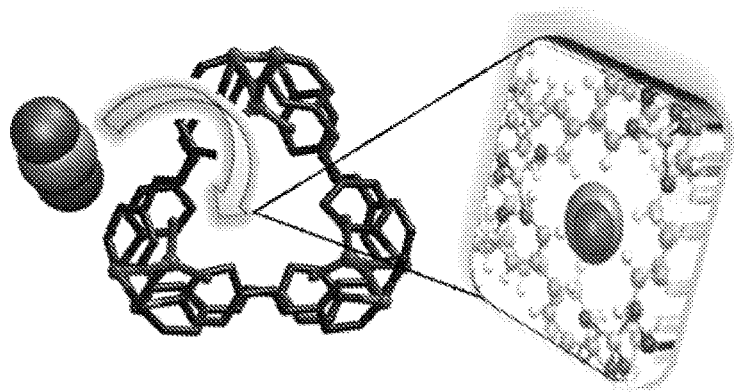
FIG. 12.1
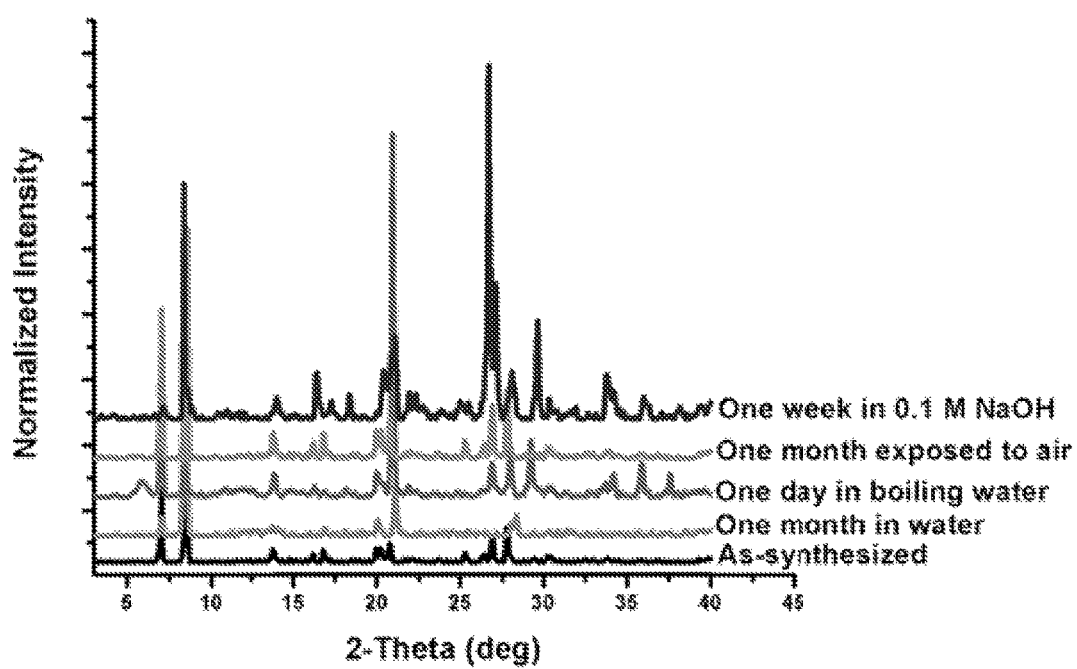
FIG. 13.1

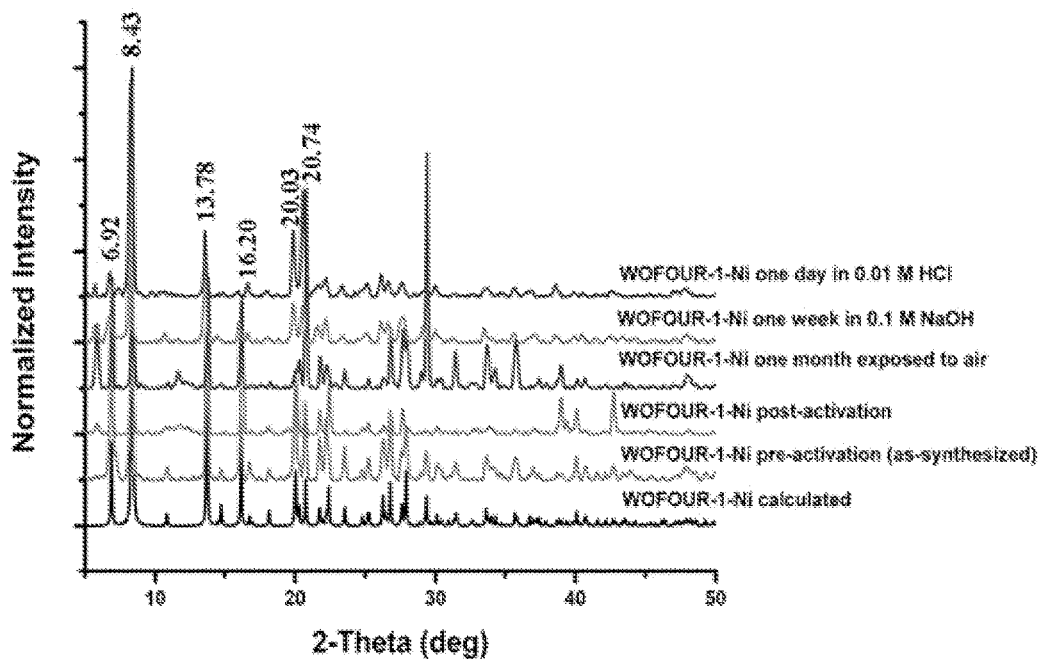
FIG. 13.2
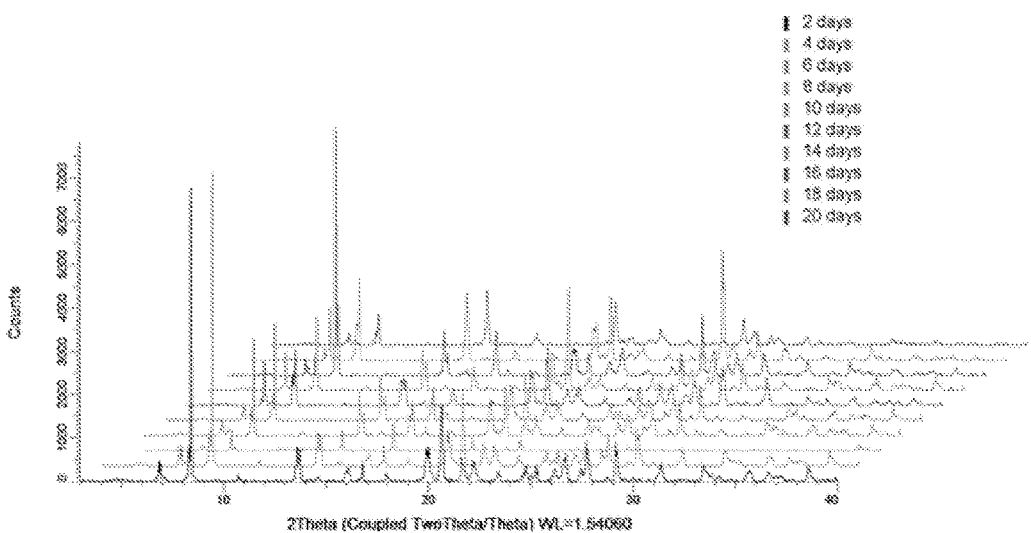
FIG. 13.3

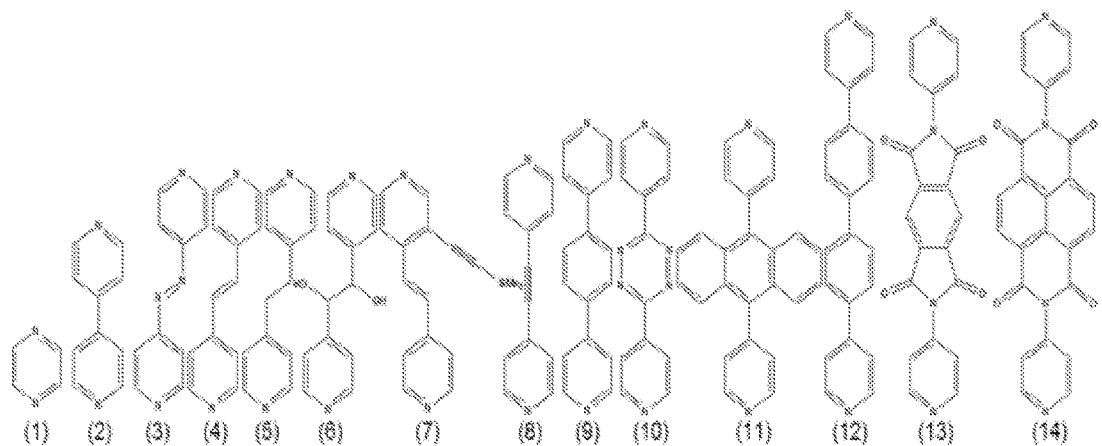
FIG. 14.1A
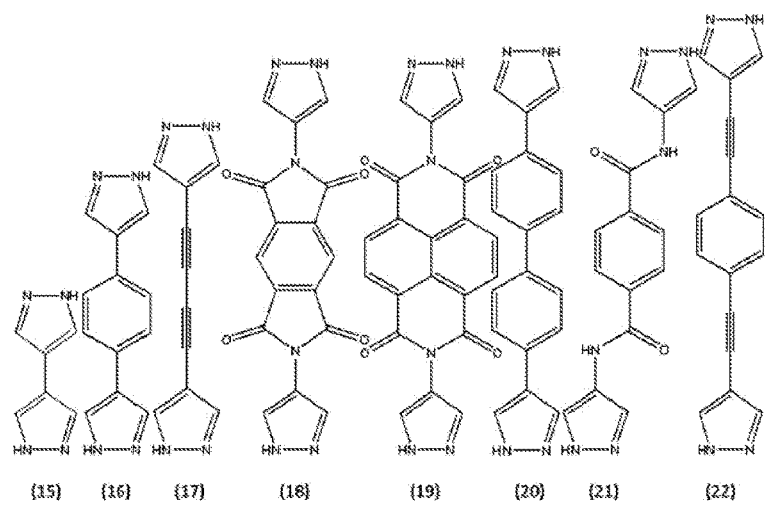
FIG. 14.1B

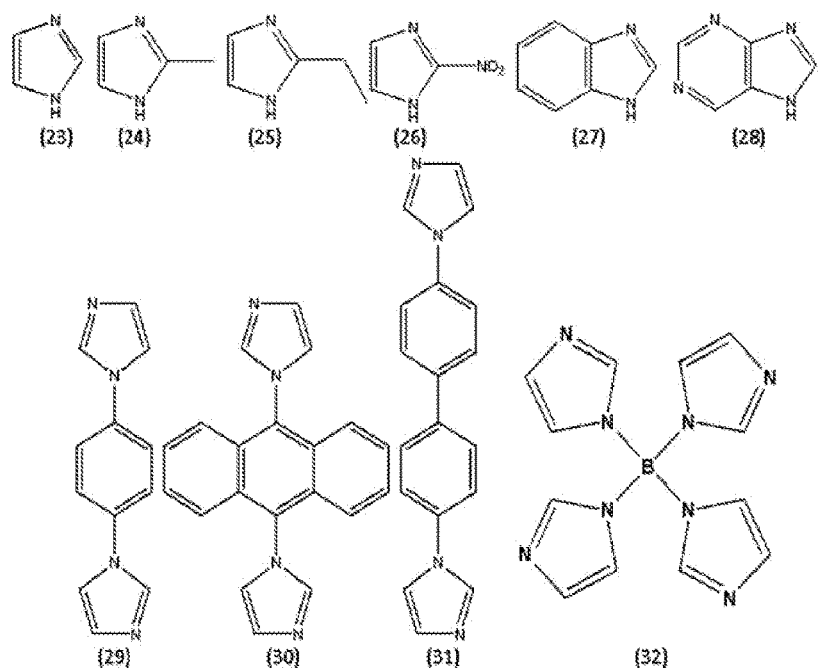
FIG. 14.1C
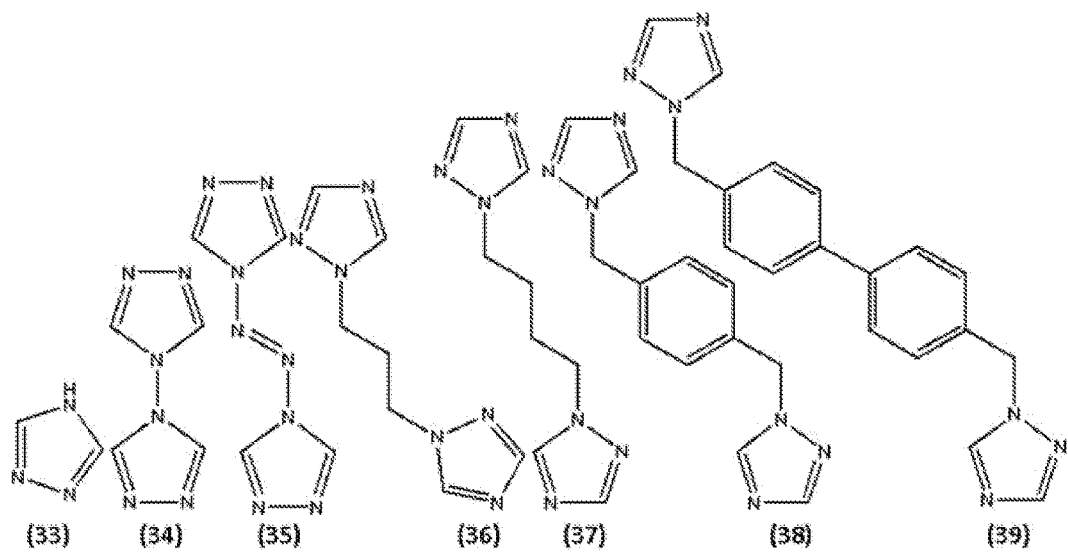
FIG. 14.1D

METAL-ORGANIC MATERIALS (MOMS) FOR ADSORPTION OF POLARIZABLE GASES AND METHODS OF USING MOMS

CROSS-REFERENCE TO RELATED APPLICATION

This application is the 35 U.S.C. §371 national stage of, and claims priority to and the benefit of, PCT application PCT/US2013/067660, filed Oct. 31, 2013, which claims priority to and the benefit of U.S. Provisional Application No. 61/723,931, filed on Nov. 8, 2012, and claims priority to and the benefit of U.S. Provisional Application No. 61/779,692, filed Mar. 13, 2013, herein incorporated by reference in their entirety.

FEDERAL SPONSORSHIP

This invention was made with Government support under Contract/Grant No. DE-AR0000177, awarded by the U.S. Department of Energy. The Government has certain rights in this invention.

BACKGROUND

Metal-organic framework (MOF) materials that exhibit permanent porosity have received extensive interest due to their potential applications for gas storage or capture. However, many of the currently used MOFs have limitations, in particular, use in humid conditions and long-term stability, and thus, other types of MOFs having more desired characteristics are needed to be used in certain applications.

SUMMARY

Embodiments of the present disclosure provide for heterometallic multi-component metal-organic materials (MOMs), systems including the MOM, systems for separating components in a gas, methods of separating polarizable gases from a gas mixture, and the like.

An embodiment of the metal-organic material (MOM), among others, includes: $[M(L)_2P]_n$, wherein $[M(L)_2P]_n$ has a 6-connected $4^8.6^7$ topology net, wherein M is selected from the group consisting of: $Cu^{2+}$, $Zn^{2+}$, $Co^{2+}$, $Ni^{2+}$, $Mn^{2+}$, $Zr^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+3}$, $Cr^{3+}$, $Ru^{3+}$ and $Co^{3+}$, wherein L is a bifunctional N donor group, and P is an oxyanion with angular geometry, and wherein n is 1 to $10^{18}$.

An embodiment of the method of capturing a polarizable gas in a gas, among others, includes: exposing the gas to a $[M(L)_2P]_n$, wherein $[M(L)_2P]_n$ has a 6-connected $4^8.6^7$ topology net, wherein M is selected from the group consisting of: $Cu^{2+}$, $Zn^{2+}$, $Co^{2+}$, $Ni^{2+}$, $Mn^{2+}$, $Zr^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+3}$, $Cr^{3+}$, $Ru^{3+}$ and $Co^{3+}$, wherein L is a bifunctional N donor group, and P is an oxyanion with angular geometry, wherein n is 1 to $10^{18}$; and capturing the polarizable gas in the MOM.

An embodiment of the system for capturing a polarizable gas in a gas, among others, includes: a first structure including to a $[M(L)_2P]_n$, wherein $[M(L)_2P]_n$ has a 6-connected $4^8.6^7$ topology net, wherein M is selected from the group consisting of: $Cu^{2+}$, $Zn^{2+}$, $Co^{2+}$, $Ni^{2+}$, $Mn^{2+}$, $Zr^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+3}$, $Cr^{3+}$, $Ru^{3+}$ and $Co^{3+}$, wherein L is a bifunctional N donor group, and P is an oxyanion with angular geometry, wherein n is 1 to $10^{18}$; and a second structure for introducing the gas to the first structure, wherein the polarizable gas is removed from the gas after the exposure to the MOM to form a modified gas, wherein the second structure flows the modified gas away from the first structure.

An embodiment of the method of separating components in a gas, among others, includes: exposing a gas including a first component and a second component to a metal-organic material (MOM), wherein the MOM includes a $[M(L)_2P]_n$, wherein $[M(L)_2P]_n$ has a 6-connected $4^8.6^7$ topology net, wherein M is selected from the group consisting of: $Cu^{2+}$, $Zn^{2+}$, $Co^{2+}$, $Ni^{2+}$, $Mn^{2+}$, $Zr^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+3}$, $Cr^{3+}$, $Ru^{3+}$ and $Co^{3+}$, wherein L is a bifunctional N donor group, and P is an oxyanion with angular geometry, wherein n is 1 to $10^{18}$, wherein the MOM has a greater relative affinity for the first component over a second component; and capturing the first component in the MOM.

An embodiment of the system for separating components in a gas, among others, includes: a first structure including to a metal-organic material (MOM), wherein the MOM includes [a $[M(L)_2P]_n$, wherein $[M(L)_2P]_n$ has a 6-connected $4^8.6^7$ topology net, wherein M is selected from the group consisting of: $Cu^{2+}$, $Zn^{2+}$, $Co^{2+}$ $Ni^{2+}$, $Mn^{2+}$, $Zr^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+3}$, $Cr^{3+}$, $Ru^{3+}$ and $Co^{3+}$, wherein L is a bifunctional N donor group, and P is an oxyanion with angular geometry, wherein n is 1 to $10^{18}$, wherein the gas includes a first component and a second component, wherein the MOM has a greater relative affinity for the first component over the second component; and a second structure for introducing the gas to the first structure, wherein first component is removed from the gas after the exposure to the hydrophobic MOM to form a modified gas, wherein the second structure flows the modified gas away from the first structure.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates a single crystal x-ray structure of MOOFOUR-1-Ni viewed along [001], H atoms omitted for clarity (left). View of the cavity of MOOFOUR-1-Ni (right).

FIG. 1.2A illustrates a topological representation of the mmo nets reported herein. FIG. 1.2B illustrates three self-catenated square grids are connected with $M'O_4^{-2}$ pillars.

FIG. 1.3 illustrates reversible single component gas adsorption isotherms for MOOFOUR-1-Ni and CROFOUR-1-Ni measured at 298K.

FIG. 1.4 illustrates $CO_2$ isosteric heats of adsorption ($Q_{st}$) of CROFOUR-1-Ni and MOOFOUR-1-Ni.

FIG. 1.5 illustrates normalized $CO_2$ dipole distribution in CROFOUR-1-Ni and MOOFOUR-1-Ni at 298 K and 0.10 atm produced from simulation. The three dimensional histograms showing the primary and secondary sites of $CO_2$ sorption are presented.

FIG. 1.6 illustrates Scheme 1, which illustrates a self-assembly of octahedral metal centers, $M'O_4^{2-}$ moieties (green) and bpe ligands affords chiral helices of metal centers and $M'O_4^{2-}$ moieties cross-linked by bpe linkers, thereby affording a 6-c mmo net.

FIG. 1.7 illustrates an infrared spectroscopy (diffuse reflectance) for CROFOUR-1-Co, CROFOUR-1-Ni, MOOFOUR-1-Co and MOOFOUR-1-Ni.

FIG. 1.8 illustrates experimental and calculated powder X-ray diffraction (PXRD) patterns for MOOFOUR-1-Co.

FIG. 1.9 illustrates experimental and calculated powder X-ray diffraction patterns of CROFOUR-1-Co.

FIG. 1.10 illustrates pre-activation and post-activation experimental and calculated powder X-ray diffraction patterns for MOOFOUR-1-Ni.

FIG. 1.11 illustrates pre-activation and post-activation experimental and calculated powder X-ray diffraction patterns for CROFOUR-1-Ni.

FIG. 1.12 illustrates PXRD patterns for MOOFOUR-1-Ni addressing its water and air stability.

FIG. 1.13 illustrates $CO_2$ isotherms of MOOFOUR-1-Ni and CROFOUR-1-Ni measured at 195 K.

FIG. 1.14 illustrates $CO_2$ adsorption isotherms of MOOFOUR-1-Ni and CROFOUR-1-Ni measured at 273 K and 283 K.

FIG. 1.15 illustrates $CO_2$ adsorption isotherms of MOOFOUR-1-Ni at 273 K and 298 K fitted using the virial equation.

FIG. 1.16 illustrates $CO_2$ adsorption isotherms of MOOFOUR-1-Ni at 273 K, 283 K and 298 K fitted using the virial equation.

FIG. 1.17 illustrates $CO_2$ isosteric heats of adsorption ($Q_{st}$) of MOOFOUR-1-Ni using the fitted data measured at two (273 K and 298 K) and three (273 K, 283 K and 273 K) temperatures.

FIG. 1.18 illustrates $CO_2$ adsorption isotherms of CROFOUR-1-Ni fitted using the virial equation.

FIG. 1.19 illustrates $CO_2$ adsorption isotherms of CROFOUR-1-Ni at 273 K, 283 K and 298 K fitted using the virial equation.

FIG. 1.20 illustrates $CO_2$ isosteric heats of adsorption ($Q_{st}$) of CROFOUR-1-Ni using the fitted data measured at two (273 K and 298 K) and three (273 K, 283 K and 273 K) temperatures.

FIG. 1.21 illustrates IAST calculated selectivity for a 50:50 $CO_2$:$CH_4$ mixture based upon the experimentally observed adsorption isotherms of the pure gases for MOOFOUR-1-Ni and CROFOUR-1-Ni.

FIG. 1.22 illustrates IAST calculated selectivity for a 10:90 $CO_2$:$N_2$ mixture based upon experimentally observed adsorption isotherms of the pure gases for MOOFOUR-1-Ni and CROFOUR-1-Ni.

FIGS. 1.23A-E illustrate adsorbed $CO_2$ molecules in MOOFOUR-1-Ni showing: 1.23A Side view of the primary binding site (site I). 1.23B Top view of the primary binding site (site I). 1.23C Side view of the secondary binding site (site II). 1.23D Top view of the secondary binding site (site II). 1.23E Side view of the both binding sites (site I and II).

FIG. 1.24 illustrates snapshot of a 1×1×2 unit cell of CROFOUR-1-Ni during the simulation showing the strong interaction between $CO_2$ molecules and 3 pairs of terminal oxygen atoms sticking out from the chromate ion (see box).

FIG. 2.1 illustrates a self-catenated square grids connected with the angular $WO_4^{-2}$ pillars to afford 6-c uninodal mmo topology net of WOFOUR-1-Ni.

FIG. 2.2 illustrates the single crystal x-ray structure of WOFOUR-1-Ni viewed along [001] (left). View of the cavity in WOFOUR-1-Ni along [001] (right). H atoms omitted for clarity.

FIG. 2.3 illustrates reversible single component gas adsorption isotherms of WOFOUR-1-Ni.

FIG. 3.1 illustrates the single crystal x-ray structure of WOFOUR-1-Co viewed along [001].

FIG. 4.1 illustrates the single crystal x-ray structure of MOOFOUR-2-Ni viewed along [001].

FIG. 5.1 illustrates the single crystal x-ray structure of CROFOUR-2-Ni viewed along [001].

FIG. 5.2 illustrates a view of the two cavities in CROFOUR-2-Ni along [001].

FIG. 5.3 illustrates reversible single component gas adsorption isotherms of CROFOUR-2-Ni.

FIG. 6.1 illustrates the single crystal x-ray structure of WOFOUR-2-Ni viewed along [001].

FIG. 7.1 illustrates the single crystal x-ray structure of WOFOUR-2-Co viewed along [001].

FIG. 8.1 illustrates the single crystal x-ray structure of CROFOUR-3-Ni viewed along [001], H atoms omitted for clarity.

FIG. 8.2 illustrates a view of the two cavities in CROFOUR-3-Ni along [001].

FIG. 8.3 illustrates reversible single component gas adsorption isotherms of CROFOUR-3-Ni.

FIG. 9.1 illustrates the single crystal x-ray structure of MOOFOUR-3-Ni viewed along [001], H atoms omitted for clarity.

FIG. 10.1 illustrates the single crystal x-ray structure of CROFOUR-4-Ni viewed along [001], H atoms omitted for clarity.

FIG. 11.1 illustrates the single crystal x-ray structure of MOOFOUR-4-Ni viewed along [001] (left). View of the cavity in MOOFOUR-4-Ni along [001] (right). H atoms omitted for clarity.

FIG. 12.1 illustrates a schematic of a MOM of the present disclosure.

FIG. 13.1 illustrates powder X-ray diffraction patterns of MOOFOUR-1-Ni addressing its stability.

FIG. 13.2 illustrates powder X-ray diffraction patterns of WOFOUR-1-Ni addressing its stability.

FIG. 13.3 illustrates PXRD patterns for WOFOUR-1-Ni addressing its stability in boiling water for up to 20 days.

FIG. 14.1A to 14.1D illustrate structures of exemplary pillars.

DISCUSSION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic chemistry, organometallic chemistry, coordination chemistry and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions:

The term "substituted" refers to any one or more hydrogens on the designated atom that can be replaced with a selection from the indicated group, provided that the designated atom's normal valence is not exceeded (though charged and radical variants are acceptable (e.g., $RNH_3^+$ versus $RNH_2$), and that the substitution results in a suitably stable compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "substituted," as in "substituted alkyl", "substituted cycloalkyl," "substituted cycloalkenyl," substituted aryl, "substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted. In an embodiment, an aryl can include a biaryl, which refers to an aryl, as defined above, where two aryl groups are joined by a direct bond or through an intervening alkyl group, preferably a lower alkyl group.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "fused aryl" refers to a aryl multicyclic ring system as included in the term "aryl," and includes aryl groups and heteroaryl groups that are condensed. Examples are naphthyl, anthryl, and phenanthryl. The bonds can be attached to any of the rings.

General Discussion:

Embodiments of the present disclosure provide for heterometallic multi-component metal-organic materials (MOMs), systems including the MOM, systems for separating components in a gas, methods of separating polarizable gases (e.g., such as $CO_2$) from a gas mixture, and the like.

MOMs of the present disclosure are inexpensive and particularly facile to synthesize. In addition, the modular nature of the MOMs of the present disclosure allows the MOMs (e.g., $[M(L)_2P]$ such as $[M(L)_2(M'O_4)]$ (M=main group metals, transition metals, lanthanides, or actinides; L=dipyridyl-type linker or other N-donor linker; $M'O_4$=angular inorganic oxyanion pillar)) to be fine-tuned at 3 sites (M, linker and M') without changing the overall structure. This allows for systematic study of structure-property relationships. Furthermore, the MOMs of the present disclosure are extraordinary stable as they retain their crystallinity in water over a wide range of pH and they are stable in air and boiling water for months (See Example 13).

In an embodiment, the MOM can be porous and can be a three dimensional net so that molecules can be disposed (e.g., captured) within (e.g., pores or cavities) the MOM to the exclusion of other molecules. In an embodiment, the MOM combines optimal sorption thermodynamics and kinetics to achieve advantageous results.

For example, a gas such as $CO_2$ is absorbed faster and stronger than other gases in the gas mixture, so that $CO_2$ can be captured in the MOMs to the substantial exclusion of the other gases such as nitrogen, oxygen, methane and water vapor. Embodiments of the present disclosure have the highest ever energies for $CO_2$ physisorption, which is an unexpected outcome as described in more detail in the Examples. This performance can be ascribed to strong quadrupole-quadrupole interactions between $CO_2$ and the metal oxide binding sites that line the pore walls.

Other polarizable gases such as nitrogen and sulfur oxides, iodine, alkenes, acetylene, and krypton can also be captured in the MOMs to the substantial exclusion of other gases such as nitrogen, oxygen, methane, and water vapor.

In an embodiment, the MOM can be used to separate $CO_2$ from one or more other gases. MOMs used in embodiments of the present disclosure can be effective at removing $CO_2$ and are highly selective in separating $CO_2$ from other gases such as $N_2$, $H_2$, and/or $CH_4$. In particular, embodiments of the present disclosure can be used in $CO_2$ capture, gas separation, and the like, in post-combustion systems (e.g., flue gas to separate $CO_2$ and $N_2$), pre-combustion systems (e.g., shifted synthesis gas stream to separate $CO_2$ and $H_2$), and/or natural gas upgrading (e.g., natural gas cleanup to separate $CO_2$ and $CH_4$). In an embodiment, the MOMs can be used to separate other gases and can be used in processes such as He separation from natural gas, Ar separation, Kr separation, $H_2/D_2$ separation, iodine separation, separation of nitrogen and sulfur oxides, and separation of unsaturated hydrocarbons from saturated hydrocarbons.

In an embodiment, the MOM has six-coordinated metal centers that serve as 6-connected (6-c) nodes and only two of the 4 oxygen atoms of each $M'O_4$ linker are coordinated; the remaining oxygen atoms are oriented towards the interior of one dimensional channels along [001]. These nets represent the first examples of 6-c $4^8.6^7$ topology nets and the symbol mmo has been assigned by RCSR. The tetrahedral $M'O_4$ pillars play a key role in directing the mmo topology as they pillar the square grids in angular fashion (112°) resulting in self-catenation of square grid nets and a helix of alternating 6-c SMCs and $M'O_4$ pillars along [001].

In an embodiment, the MOM can be a metal organic framework. In an embodiment, the MOM (e.g., $[Co(bpe)_2(MoO_4)]_n$) can be designed and synthesized using grids (or 2D nets) (e.g., $Co(bpe)_2$) that are linked via metal nodes using a pillar (e.g., $MoO_4^{2-}$). In an embodiment, the grids include metal cations, metal cluster molecular building blocks (MBBs), or metal-organic polyhedral supermolecular building blocks (SBBs). The MBBs or SBBs serve the geometric role of the node in a network and they are connected by organic molecules, inorganic anions and/or metal complexes, which serve as linkers. The grids are connected to one another using other linkers or pillars that connect the metal nodes.

In an embodiment, the MOM can have the following generic structure having 6-c $4^8.6^7$ topology: $[M(L)_2P]_n$, where M is the metal node, L is a linear linker (e.g., bifunctional N donors), and P is an angular pillars (e.g., oxyanions with angular geometry), and wherein n can be 1 to $10^{18}$. In an embodiment, M can include $Cu^{2+}$, $Zn^{2+}$, $Co^{2+}$, $Ni^{2+}$, $Mn^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Zr^{2+}Mg^{+2}$, $Al^{+3}$, $Fe^{+3}$, $Cr^{3+}$, $Ru^{3+}$ and $Co^{3+}$. In an embodiment, M can be $Co^{2+}$ or $Ni^{2+}$. In an embodiment, P can include $CrO_4^{2-}$, $MoO_4^{2-}$, $WO_4^{2-}$, $SO_4^{2-}$, $TiO_4^{2-}$, $SeO_4^{2-}$, $CO_3^{2-}$, $SO_3^{2-}$, $SiO_3^{2-}$, $ZrO_3^{2-}$, $Cr_2O_7^{2-}$, $Mo_2O_7^{2-}$, $S_2O_3^{2-}$, $S_2O_6^{2-}$, $S_2O_8^{2-}$, $Ti_3O_7^{2-}$, $PO_4^{3-}$, $VO_4^{3-}$, $AsO_4^{3-}$, $PO_3^{3-}$, $BO_3^{3-}$, $AsO_3^{3-}$, and the like. In an embodiment, L can be a dipyridyl-based linker, a pyrazolate-based linker, a imidazolate-based linker, a tetrazolate-based linker or a triazolate-based linker. In an embodiment, FIGS. 14.1A to 14.1D illustrate embodiments of dipyridyl-based linkers, pyrazolate-based linkers, imidazolate-based linkers, or triazolate-based linkers, respectively, where each H in each of these structures can be independently substituted with: a substituted or unsubstituted aliphatic group, a substituted or unsubstituted alkyl, a substituted or unsubstituted cycloalkyl, a substituted or unsubstituted alkenyl, a substituted or unsubstituted cycloalkenyl, a substituted or unsubstituted alkynyl, a substituted or unsubstituted aryl, a halo group, or a substituted or unsubstituted araalkyl.

As shown in FIGS. 14.1A to 14.1D, the structures can have the following names: (1) pyrazine, (2) 4,4'-bipyridine, (3) 4,4'-azo-bis(pyridine), (4) 1,2-bis(4-pyridyl)ethene, (5) 1,2-bis(4-pyridyl)ethane, (6) 1,2-di(pyridine-4-yl)ethane-1,2-diol, (7) 3-[(trimethylsilyl)ethynyl]-4-[2-(4-pyridinyl)ethenyl]pyridine, (8) 1,2-bis(4-pyridyl)ethyne, (9) 1,4-bis(4-pyridyl)benzene, (10) 3,6-di(pyridin-4-yl)-1,2,4,5-tetrazine, (11) 4-(9-(pyridin-4-yl)anthracen-10-yl)pyridine, (12) 4,4'-bis(4-pyridyl)biphenyl, (13) N,N'-bis(4-pyridyl)pyromellitic diimide, (14) N,N'-di(pyridyl)-1,4,5,8-naphthalenetetracarboxydiimide, (15) 4,4'-bipyrazolyl, (16) 1,4-bis(1H-pyrazol-4-yl)benzene, (17) 4,4'-buta-1,3-diyne-1,4-diylbis(1H-pyrazole), (18) N,N'-bis(1H-pyrazol-4-yl)pyromellitic diimide, (19) N,N'-bis(1H-pyrazol-4-yl)-1,4,5,8-naphthalenetetracarboxydiimide, (20) 4,4'-bis(1H-pyrazol-4-yl)biphenyl, (21) N,N'-bis(1H-pyrazol-4-yl)-1,4-benzenedicarboxamide, (22) 4,4'-benzene-1,4-diylbis(1H-pyrazole), (23) Imidazole, (24) 2-methylimidazole, (25) 2-ethylimidazole, (26) 2-nitroimidazole, (27) benzimidazole, (28) purine, (29) 1,4-bis(1-imidazolyl)benzene, (30) 9,10-(1-imidazolyl)anthracene, (30) 4,4'-bis(1-imidazolyl)biphenyl, (32) tetrakis(1-Imidazolyl)borate, (33) 1,2,4-triazol, (34) 4,4'-bis-1,2,4-triazol, (35) 4,4'-azo-1,2,4-triazol, (36) 1,3-bis(1,2,4-triazol-1-yl)-propane, (37) 1,4-bis(1,2,4-triazol-1-yl)-butane, (38) 1,4-bis(1,2,4-triazol-1-ylmethyl)-benzene, and (39) 4,4'-bis(1,2,4-triazol-1-ylmethyl)-1,1'-biphenyl.

In a specific embodiment, the $[M(L)_2P]$ can have the following structure: $[M(L)_2(M'O_4)]_n$, where n is 1 to $10^{18}$. In an embodiment, the MOM has a 6-connected $4^8.6^7$ topology net. In an embodiment, M Can include $Cu^{2+}$, $Zn^{2+}$, $Co^{2+}$, $Ni^{2+}$, $Mn^{2+}$, $Mo^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Zr^{2+}$, $Mg^{+2}$, $Al^{+3}$, $Fe^{+3}$, $Cr^{3+}$, $Ru^{3+}$ and $Co^{3+}$. In an embodiment, M' can include $CrO_4^{2-}$, $MoO_4^{2-}$, $WO_4^{2-}$, $SO_4^{2-}$, $TiO_4^{2-}$, $SeO_4^{2-}$, $CO_3^{2-}$, $SO_3^{2-}$, $SiO_3^{2-}$, $ZrO_3^{2-}$, $Cr_2O_7^{2-}$, $Mo_2O_7^{2-}$, $S_2O_3^{2-}$, $S_2O_6^{2-}$, $S_2O_8^{2-}$, $Ti_3O_7^{2-}$, $PO_4^{3-}$, $VO_4^{3-}$, $AsO_4^{3-}$, $PO_3^{3-}$, $BO_3^{3-}$, $AsO_3^{3-}$, and the like. In an embodiment, M and M' are different. In an embodiment, M can be Co or Ni. In an embodiment, M' can be Mo, W, or Cr. In an embodiment, L can be any linker as described herein or in reference to FIGS. 14.1A to 14.1D and the like.

In an exemplary embodiment, the MOM can include: $[Co(bpe)_2(CrO_4)]$, $[Ni(bpe)_2(CrO_4)]_n$, $[Ni(bpa)_2(CrO_4)]_n$, $[Ni(zbp)_2(CrO_4)]_n$, $[Ni(bpb)_2(CrO_4)]_n$, $[Co(bpe)_2(MoO_4)]_n$, $[Ni(bpe)_2(MoO_4)]_n$, $[Ni(bpa)_2(MoO_4)]_n$, $[Ni(zbp)_2(MoO_4)]_n$, $[Ni(bpb)_2(MoO_4)]_n$, $[Co(bpe)_2(WO_4)]_n$, $[Ni(bpe)_2(WO_4)]_n$, $[Co(bpa)_2(WO_4)]_n$, and $[Ni(bpa)_2(WO_4)]_n$, wherein n is 1 to $10^{18}$. Additional details regarding these heterometallic MOMs are provided in the Examples.

In an embodiment, the components of the MOM can be selected to design a MOM that can be used in a system or method that is highly effective at separating gases due to the MOM having a higher relative affinity for one polarizable component of the gas (e.g., $CO_2$) over one or more other components (e.g., $N_2$, $H_2$, and $CH_4$) in the gas.

In an embodiment, a method of the present disclosure includes exposing a gas to a multi-component MOM as described herein. As noted above, the MOM has a greater relative affinity for a first component of the gas over a second component of the gas. The phrase "greater relative affinity" or similar phrases mean that a MOM can interact with a first component much more strongly than a second component so that the MOM and the first component interact to the substantial exclusion of the second component. In an embodiment, the affinity can be controlled by linkers in the MOM that exhibit strong enough electrostatic potential to induce polarization in one component of the gas. Thus, the first component can be captured (e.g., separated) from the gas mixture to form a modified gas, where the modified gas includes the second component and a substantially reduced amount (e.g., greater than about 80% or more, about 90% or more, about 95% or more, about 99% or more, about 99.9% or more, removal of the first component from the gas) of the first component.

In an embodiment, the gas can include two or more components. In an embodiment, the component can include one or more of the following: $CO_2$, $N_2$, $H_2$, $CH_4$, He, hydrocarbons having 2 or more carbons (saturated or unsaturated and/or linear or branched), rare gases, nitrogen oxides, sulfur oxides and a combination thereof. In an embodiment, $CO_2$ can be in the gas in an amount of about 400 ppm to 50%. In an embodiment, $N_2$ can be in the gas in an amount of about 50% to 99.99%. In an embodiment, $H_2$ can be in the gas in an amount of about 50% to 99.99%. In an embodiment, $CH_4$ can be in the gas in an amount of about 50% to 99.99%. In an embodiment, He can be in the gas in an amount of about 50% to 99.99%.

It should be noted that in many situations, the gas may primarily include a few components or only a few components that are important to the desired separation. For example, in post-combustion systems such as one that contains flue gas, the two main components for separation are $CO_2$ and $N_2$. In another example, in pre-combustion systems such as shifted synthesis gas streams, the two main components to separate are $CO_2$ and $H_2$. In another embodiment, in natural gas upgrading systems such as natural gas cleanup, the two main components to separate are $CO_2$ and $CH_4$. In another embodiment, in a He separation system, the two main components to separate are He and natural gas.

In an embodiment, the components in a gas can be separated using a system to introduce the gas to the MOM and remove the modified gas. In an embodiment, a first structure or device including the MOM can be interfaced with a second structure or device to introduce a gas to the first structure so that the gas and the MOM can interact so that the MOM can capture the first component (e.g., $CO_2$). After a sufficient period of time and under appropriate temperature conditions, the remaining gas or modified gas can be removed from the first structure. This process can be repeated as appropriate for the particular system. After a period of time, the first component can be removed from the MOM and the MOM can be reused and/or recycled using an appropriate gas handling system.

In an embodiment, the first structure and the second structure can include those used in systems such as post-combustion systems, pre-combustion systems, natural gas upgrading systems, and separation systems. In particular, the first structure can include structures such as those used in typical systems mentioned above. In an embodiment, the second structure can include standard gas handling systems, valves, pumps, flow meters, and the like.

As mentioned above, the separation method or system using the MOMs can be used to selectively remove $CO_2$ from $N_2$, $H_2$, and/or $CH_4$. In an embodiment, the selectivity for $CO_2/N_2$ can be about 100 or more, about 500 or more, about 1000 or more, or about 2000 or more, based on ideal absorbed solution theory (IAST) calculations conducted using experimental data (described in greater detail in the Example) and at conditions similar to those described in the Example.

In an embodiment, the selectivity for $CO_2/CH_4$ can be about 100 or more, about 500 or more, about 1000 or more, or about 2000 or more, based on IAST calculations (described in greater detail in the Example) and at conditions of similar to those described in the Example.

EXAMPLE

Now having described the embodiments of the present disclosure, in general, the Examples describe some additional embodiments of the present disclosure. While embodiments of present disclosure are described in connection with the Examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Brief Introduction:

A novel $4^8.6^7$ topology metal organic material (MOM) of formula [M(bpe)$_2$(M'O$_4$)] (M=Co or Ni; bpe=1,2-bis(4-pyridyl)ethene; M'=Mo or Cr) has been synthesized and evaluated in the context of gas sorption. These MOMs have been assigned RCSR code mmo and are uninodal 6-connected nets. [Ni(bpe)$_2$(MoO$_4$)], MOOFOUR-1-Ni, and its chromate analog, CROFOUR-1-Ni, exhibit high CO$_2$ affinity and selectivity, especially at low loading. This behavior can be attributed to exceptionally high isosteric heats of adsorption ($Q_{st}$) of CO$_2$ in MOOFOUR-1-Ni and CROFOUR-1-Ni of ~56 and ~50 kJ/mol, respectively, at zero loading. These results were validated by molecular simulations which indicate that the electrostatics of these inorganic anions affords attractions towards CO$_2$ that are comparable to those of unsaturated metal centers.

Discussion:

Metal organic materials (MOMs) are typically comprised from metal ions or metal clusters with 3 or more points of connection (nodes) and organic ligands or metal clusters that serve as linkers.[1] MOMs have emerged as a class of porous materials with great potential for a wide range of applications, including gas storage,[2] heterogeneous catalysis,[3] drug delivery,[4] magnetism[5] and conductivity.[6] The drive behind the development of MOMs is their well-defined crystal structure, extraordinary surface area and their modular nature, which makes for tunable pore dimensions and surfaces.[7]

We report herein a new variant of a well-established crystal engineering[8] approach for building porous MOMs: pillaring of [M(bpy)$_2$] (bpy=4,4-pyridine) square grids[9] with inorganic anions.[10] The prototypal nets contain saturated metal centers (SMCs) and exhibit pcu topology when anions such as SiF$_6^{2-}$ and PF$_6^-$ serve as linear linkers.[10a,b,11] They represent ideal families or platforms to test the effect of pore size upon gas sorption behavior since the bpy linkers can be expanded (e.g. 1,4-bis(4-pyridyl)benzene)[12] or contracted (e.g. pyrazine)[13] quite readily. Such an approach allows for systematic control of pore size to optimize interactions between the framework and the adsorbent in order to enhance selectivity and/or gas uptake. Other strategies for enhancement of sorbent/sorbate interactions such as unsaturated metal centers (UMCs),[14] basic nitrogen atoms,[15] alkylamine,[16] amide groups,[17] or ion-exchange[18] have been reported. We herein describe a new platform based upon pillaring of [M(bpe)$_2$] square grids by angular MoO$_4^{2-}$ or CrO$_4^{2-}$ pillars (scheme 1). Such pillars are underexplored in MOMs. Indeed, there are just three reports concerning MoO$_4^{-2}$ acting as a linker[19] whereas there are no examples reported for CrO$_4^{-2}$. [M(bpe)$_2$(M'O$_4$)] (M=Co, Ni; M'=Mo, Cr), have been synthesized, structurally characterized and evaluated in terms of their sorption behavior with respect to three industrially important gases CO$_2$, CH$_4$ and N$_2$. [M(bpe)$_2$(M'O$_4$)] (M=Co, Ni; M'=Mo, Cr) were synthesized at room temperature by dissolving CoCl$_2$ (or NiCl$_2$) and Na$_2$MoO$_4$ (or K$_2$CrO$_7$) in water and layering the resulting solution under bpe in water/acetonitrile. Single crystals of [Co(bpe)$_2$MoO$_4$] (MOOFOUR-1-Co), [Ni(bpe)$_2$MoO$_4$] (MOOFOUR-1-Ni) [Co(bpe)$_2$CrO$_4$] (CROFOUR-1-Co) and [Ni(bpe)$_2$CrO$_4$] (CROFOUR-1-Ni) were thereby afforded. Crystal structures were determined by single crystal X-ray diffraction which revealed that all four compounds crystallize in the chiral space group R32 with one formula unit per unit cell. The six-coordinated metal centers serve as 6-connected (6-c) nodes and only two of the 4 oxygen atoms of each M'O$_4$ linker are coordinated; the remaining oxygen atoms are oriented towards the interior of one dimensional channels along [001] (FIG. 1.1). To our knowledge, these nets represent the first examples of 6-c $4^8.6^7$ topology nets[20] and the symbol mmo has been assigned by RCSR[21] (FIG. 1.2A-B). The tetrahedral M'O$_4$ pillars play a key role in directing the mmo topology as they pillar the square grids in angular fashion (112°) resulting in self-catenation[1d,22] of square grid nets and a helix of alternating 6-c SMCs and M'O$_4$ pillars along [001] (scheme 1 in FIG. 1.6). This platform represents a new heterometallic class of MOMs that complements those reported recently through an approach based upon heterometallic clusters.[23]

The affinity of anions such as SiF$_6^{2-}$ and PF$_6^-$ towards CO$_2$[24,25] prompted us to evaluate the gas sorption properties of MOOFOUR-1-Ni and CROFOUR-1-Ni. Permanent porosity was confirmed via CO$_2$ adsorption measurements at 195 K and Langmuir surface areas of 456 m$^2$/g and 505 m$^2$/g were determined for MOOFOUR-1-Ni and CROFOUR-1-Ni, respectively. CO$_2$, CH$_4$ and N$_2$ adsorption isotherms were measured at 298 K and reveal unexpectedly high affinity towards CO$_2$ as exemplified by the steep CO$_2$ uptakes in the low pressure regions compared to CH$_4$ and N$_2$ (FIG. 1.3). The CO$_2$ uptake of MOOFOUR-1-Ni at 1 atm is 55 cm$^3$/g whereas that of CROFOUR-1-Ni is 43 cm$^3$/g. The CH$_4$ and N$_2$ uptakes for MOOFOUR-1-Ni and CROFOUR-1-Ni are 11.5 cm$^3$/g, 4.5 cm$^3$/g and 13 cm$^3$/g, 4 cm$^3$/g, respectively. MOOFOUR-1-Ni therefore outperforms CROFOUR-1-Ni despite its higher density, which, given that this is an "apple v. apple" comparison, suggests that MoO$_4^{2-}$ exhibits a stronger binding affinity for CO$_2$ than CrO$_4^{2-}$.

In order to rationalize these observations, the isosteric heat of adsorption ($Q_{st}$) of CO$_2$ for both structures was calculated using adsorption data at 273 K, 283 K and 298 K according to the virial equation. FIG. 1.4 reveals that the $Q_{st}$ of MOOFOUR-1-Ni is at least 5 kJ/mol>CROFOUR-1-Ni across all loadings. The Qst values of MOOFOUR-1-Ni and CROFOUR-1-Ni are ~56 and ~50 kJ/mol, respectively, at zero loading although they decrease to ~33 and ~27 kJ/mol, respectively, at 1 atm. To put this in perspective, both compounds exhibit higher Qst values at low loading than MOMs with UMCs such as HKUST-1,[26] MIL-53 (Al),[27] Mg-MOF-74,[28] Co-MOF-74[28] and Ni-MOF-74[28] which exhibit values of 30, 35, 47, 37, 41 kJ/mol, respectively. They also surpass NaY[29] (36 kJ/mol), zeolite 13X[30] (40 kJ/mol) and a number of MOFs with amine-group ligands (35-45 kJ/mol).[31,32] A value of 45 kJ/mol has been reported for a MOM in which phosphonate monoester linkers afford confined space.[33]

$Q_{st}$ values of >40 kJ/mol would be expected to afford high selectivity for CO$_2$ vs. CH$_4$ and N$_2$. CO$_2$/CH$_4$ molar selectivity for a 50:50 mixture was calculated by IAST to be 182 and 170 for MOOFOUR-1-Ni and CROFOUR-1-Ni, respectively, at zero coverage. The corresponding values at 1 atm were found to be 40 and 25. The CO$_2$/N$_2$ selectivity for a 10:90 mixture, which represents a typical composition for flue gas from power plants, was 1820 and 1240 for MOOFOUR-1-Ni and CROFOUR-1-Ni, respectively, at zero loading. These values decrease to 86 and 195 at 1 atm (supporting information). Whereas there are MOMs that exhibit a higher uptake capacity for CO$_2$, we are unaware of any that exhibit such high selectivity at low loading. We also calculated the CO$_2$/N$_2$ gravimetric selectivity in the context of post-combustion CO$_2$ capture by determining wt % at 0.15 bar and 0.75 bar for CO$_2$ and N$_2$, respectively, at ambient temperature.[2c] The wt % of CO$_2$ at 0.15 bar in MOOFOUR-1-Ni and CROFOUR-1-Ni was 5.2% and 4.6%, respectively, whereas for $N_2$ at 0.75 bar values were found to be 0.39% and 0.37%, respectively. Therefore, the selectivity of $CO_2$ over $N_2$ in MOOFOUR-1-Ni and CROFOUR-1-Ni under these conditions was found to be 67 and 62. These values exceed those of most MOMs that contain UMCs including Mg-MOF-74 (44 at 303 k)[34] and amine grafted MOMs.[16a]

The high affinity and selectivity towards $CO_2$ exhibited by MOOFOUR-1-Ni and CROFOUR-1-Ni was addressed through molecular simulations involving explicit polarization for $CO_2$ adsorption in CROFOUR-1-Ni and MOOFOUR-1-Ni to identify the most favorable sorption sites. Similar assessments have been performed for $H_2$ adsorption in MOMs.[35,36] Examination of the distribution of induced dipoles for $CO_2$ molecules in CROFOUR-1-Ni and MOOFOUR-1-Ni revealed two distinct regions of occupancy inside the MOMs. FIG. 1.5 presents a plot of the $CO_2$ dipole magnitudes against the normalized $CO_2$ population in both compounds. In MOOFOUR-1-Ni, the peak from 0.60 D to 0.70 D corresponds to the primary sorption site that is located within the region where three pairs of terminal oxygen atoms extend from their respective metal ions. This is the energetically favorable site to which the $CO_2$ molecules bind initial loading. The primary sorption site for CROFOUR-1-Ni is similar, although the magnitudes of the dipoles are slightly lower, ranging from 0.55 D to 0.65 D.

The simulations therefore indicate that MOOFOUR-1-Ni induces higher dipoles on the $CO_2$ molecules upon adsorption, presumably due to the higher polarizability of $Mo^{VI}$ cations. In addition, a larger peak is seen for MOOFOUR-1-Ni relative to CROFOUR-1-Ni indicating higher occupancy of $CO_2$ molecules onto this primary sorption site. For both compounds, a peak from 0.05 D to 0.20 D is also observed corresponding to a secondary sorption site located within the channel next to the primary sorption site. Specifically, $CO_2$ molecules bind to the region where two different terminal oxygen atoms from their respective ions form an apex within the channel. The geometries of the adsorbed carbon dioxide molecules (sites I and II) with respect to the MOOFOUR-1-Ni host structure are shown in supporting information.

We addressed the stability of MOOFOUR-1-Ni and CROFOUR-1-Ni by confirming that as prepared samples retain crystallinity even when immersed in water for months, boiling water for one day or 0.1 N NaOH for a week (supporting information). Samples also retain their porosity after activation and being exposed to the atmosphere.

In conclusion, we have synthesized a new class of porous MOM platforms based upon SMCs and $MoO_4^{2-}$ or $CrO_4^{2-}$ as inorganic anion pillars. They exhibit a novel 6-c uninodal topology, mmo, which facilitates evaluation of $MoO_4^{2-}$ and $CrO_4^{2-}$ in terms of their effect upon gas sorption. MOOFOUR-1-Ni and CROFOUR-1-Ni were found to exhibit exceptional $Q_{st}$ and highly selective adsorption for $CO_2$ over $N_2$ and $CH_4$ and we ascribe this behavior to strong quadrupole-quadrupole interactions between $CO_2$ and $MoO_4^{2-}$ (MOOFOUR-1-Ni) and $CrO_4^{2-}$ (CROFOUR-1-Ni) binding sites. These inexpensive, facile to synthesize and robust $CO_2$ adsorbents outperform many other MOMs, even these with UMCs or amine functionalized MOMs. A wide range of other inorganic anions can serve as nodes and a wide range of linear linkers and angular pillars are readily available. References, each of which is incorporated herein by reference (1) (a) Moulton, B.; Zaworotko, M. *J. Chem. Rev.* 2001, 101, 1629; (b) Batten, S. R.; Neville, S. M.; Turner, D. R. *Coordination polymers: design, analysis and application*; Royal Society of Chemistry: Cambridge, 2009; (c) Macgillivray, L. R. *Metal-Organic Frameworks: Design and Application*; John Wiley & Sons: Hoboken, 2010; (d) Batten, S. R.; Robson, R. *Angew. Chem., Int. Ed.* 1998, 37, 1460; (e) Blake, A. J.; Champness, N. R.; Hubberstey, P.; Li, W.-S.; Withersby, M. A.; Schröder, M. *Coord. Chem. Rev.* 1999, 183, 117.

(2) (a) Li, J.-R.; Kuppler, R. J.; Zhou, H.-C. *Chem. Soc. Rev.* 2009, 38, 1477(b) Suh, M. P.; Park, H. J.; Prasad, T. K.; Lim, D.-W. *Chem. Rev.* 2012, 112, 782; (c) Sumida, K.; Rogow, D. L.; Mason, J. A.; McDonald, T. M.; Bloch, E. D.; Herm, Z. R.; Bae, T.-H.; Long, J. R. *Chem. Rev.* 2012, 112, 724.

(3) Lee, J.; Farha, O. K.; Roberts, J.; Scheidt, K. A.; Nguyen, S. T.; Hupp, J. T. *Chem. Soc. Rev.* 2009, 38, 1450.

(4) (a) Horcajada, P.; Gref, R.; Baati, T.; Allan, P. K.; Maurin, G.; Couvreur, P.; Férey, G.; Morris, R. E.; Serre, C. *Chem. Rev.* 2012, 112, 1232; (b) McKinlay, A. C.; Morris, R. E.; Horcajada, P.; Férey, G.; Gref, R.; Couvreur, P.; Serre, C. *Angew. Chem., Int. Ed.* 2010, 49, 6260.

(5) (a) Kurmoo, M. *Chem. Soc. Rev.* 2009, 38, 1353; (b) Weng, D.-F.; Wang, Z.-M.; Gao, S. *Chem. Soc. Rev.* 2011, 40,3157.

(6) Givaja, G.; Amo-Ochoa, P.; Gómez-Garcia, C. J.; Zamora, F. *Chem. Soc. Rev.* 2012, 41, 115.

(7) (a) Zeitler, T. R.; Allendorf, M. D.; Greathouse, J. A. *J. Phys. Chem. C* 2012, 116, 3492; (b) Banerjee, R.; Furukawa, H.; Britt, D.; Knobler, C.; O'Keeffe, M.; Yaghi, O. M. *J. Am. Chem. Soc.* 2009, 131, 3875; (c) Kitagawa, S.; Noro, S.-i.; Nakamura, T. *Chem. Commun.* 2006, 701; (d) Kawano, M.; Kawamichi, T.; Haneda, T.; Kojima, T.; Fujita, M. *J. Am. Chem. Soc.* 2007, 129, 15418; (e) Wang, Z.; Cohen, S. M. *J. Am. Chem. Soc.* 2009, 131, 16675; (g) Rosseinsky, M. *J. Nature Mater.* 2010, 9, 609.

(8) Desiraju, G. R. *Angew. Chem. Int. Ed.* 2007, 46, 8342.

(9) Abrahams, B. F; Hoskins, B. F.; Robson, R. *J. Am. Chem. Soc.* 1991, 113, 3606; (b) Kitagawa, S.; Kitaura, R.; Noro, S.-i. *Angew. Chem. Int. Ed.* 2004, 43, 2334; (c) Robinson, F.; Zaworotko, M. J. *J. Chem. Soc.-Chem. Commun* 1995, 2413; (d) Fujita, M.; Kwon, Y. J.; Washizu, S.; Ogura, K. *J. Am. Chem. Soc.* 1994, 116, 1151.

(10)(a) Subramanian, S.; Zaworotko, M. J. *Angew. Chem., Int. Ed.* 1995, 34, 2561; (b) Lin, M.-J.; Jouaiti, A.; Kyritsakas, N.; Hosseini, M. W. *CrystEngComm* 2011, 13, 776; (c) Kopf, A.; Maggard, P. A.; Stern, C. L.; Poeppelmeier, K. R. *Acta Cryst. C* 2005, C61, m165.

(11) Noro, S.-i.; Kitaura, R.; Kondo, M.; Kitagawa, S.; Ishii, T.; Matsuzaka, H.; Yamashita, M. *J. Am. Chem. Soc.* 2002, 124, 2568.

(12) Lin, M. J.; Jouaiti, A.; Kyritsakas, N.; Hosseini, M. W. *CrystEngComm* 2009, 11, 189.

(13) Uemura, K.; Maeda, A.; Maji, T. K.; Kanoo, P.; Kita, H. *Eur. J. Inorg. Chem.* 2009, 2329.

(14) (a) Chen, B.; Ockwig, N. W.; Millward, A. R.; Contreras, D. S.; Yaghi, O. M. *Angew. Chem., Int. Ed.* 2005, 44, 4745 (b) Wang, X.-S.; Ma, S.; Forster, P. M.; Yuan, D.; Eckert, J.; López, J. J.; Murphy, B. J.; Parise, J. B.; Zhou, H.-C. *Angew. Chem., Int. Ed.* 2008, 47, 7263; (c) Britt, D.; Furukawa, H.; Wang, B.; Glover, T. G.; Yaghi, O. M. *Proc. Natl. Acad. Sci.* 2009, 106, 20637.

(15) Lin, J.-B.; Zhang, J.-P.; Chen, X.-M. *J. Am. Chem. Soc.* 2010, 132, 6654; (b) Lin, Q.; Wu, T.; Zheng, S.-T.; Bu, X.; Feng, P. *J. Am. Chem. Soc.* 2012, 134, 784.

(16) Demessence, A.; D'Alessandro, D. M.; Foo, M. L.; Long, J. R. *J. Am. Chem. Soc.* 2009, 131, 8784; (b) Vaidhyanathan, R.; Iremonger, S. S.; Shimizu, G. K. H.; Boyd, P.; Alavi, S.; Woo, T. K. *Science*, 2010, 330, 650.

(17) Zheng, B.; Bai, J.; Duan, J.; Wojtas, L.; Zaworotko, M. J. *J. Am. Chem. Soc.* 2010, 133, 748.

(18) Maji, T. K.; Matsuda, R.; Kitagawa, S. *Nat. Mater.* 2007, 6, 142.

(19) (a) Laskoski, M. C.; LaDuca Jr, R. L.; Rarig Jr, R. S.; Zubieta, J. *J. Chem. Soc., Dalton Trans.* 1999, 3467; (b) LaDuca Jr, R. L.; Desiak, M.; Rarig Jr, R. S.; Zubieta, J. *Inorganica Chimica Acta* 2002, 332, 79; (c) Gong, Y.; Liu, T.; Tang, W.; Wu, F.; Gao, W.; Hu, C. *J. Solid State Chem.* 2007, 180, 1476.

(20) Blatov, V. A. *IUCr CompComm Newsletter* 2006, 7, 4; http://www.topos.samsu.ru.

(21) O'Keeffe, M.; Peskov, M. A.; Ramsden, S. J.; Yaghi, O. M. *Acc. Chem. Res.* 2008, 41, 1782; (b) O'Keeffe, M.; Yaghi, O. M. *Chem. Rev.* 2012, 112, 675.

(22) Carlucci, L.; Ciani, G.; Proserpio, D. M. *Coord. Chem. Rev.* 2003, 246, 247.

(23) (a) Zheng, S.-T.; Wu, T.; Chou, C.; Fuhr, A.; Feng, P.; Bu, X. *J. Am. Chem. Soc.* 2012, 134, 4517; (b) Zheng, S.-T.; Mao, C.; Wu, T.; Lee, S.; Feng, P.; Bu, X. *J. Am. Chem. Soc.* 2012, 134, 11936.

(24) (a) Noro, S.; Kitagawa, S.; Kondo, M.; Seki, K. *Angew. Chem., Int. Ed.* 2000, 39, 2082; (b) Burd, S. D.; Ma, S.; Perman, J. A.; Sikora, B. J.; Snurr, R. Q.; Thallapally, P. K.; Tian, J.; Wojtas, L.; Zaworotko, M. J. *J. Am. Chem. Soc.* 2012, 134, 3663.

(25) Noro, S.-i.; Tanaka, D.; Sakamoto, H.; Shimomura, S.; Kitagawa, S.; Takeda, S.; Uemura, K.; Kita, H.; Akutagawa, T.; Nakamura, T. *Chem. Mat.* 2009, 21, 3346.

(26) Cavenati, S.; Grande, C. A.; Rodrigues, A. E. *Ind. Eng. Chem. Res.* 2008, 47, 6333.

(27) Bourrelly, S.; Llewellyn, P. L.; Serre, C.; Millange, F.; Loiseau, T.; Férey, G. *J. Am. Chem. Soc.* 2005, 127, 13519.

(28) Caskey, S. R.; Wong-Foy, A. G.; Matzger, A. J. *J. Am. Chem. Soc.* 2008, 130, 10870.

(29) Harlick, P. J. E.; Tezel, F. H. *Micro. Meso. Mater.* 2004, 76, 71.

(30) Cavenati, S.; Grande, C. A.; Rodrigues, A. E. *J. Chem. Eng. Data* 2004, 49, 1095.

(31) Vaidhyanathan, R.; Iremonger, S. S.; Dawson, K. W.; Shimizu, G. K. H. *Chem. Commun.* 2009, 5230.

(32) An, J.; Geib, S. J.; Rosi, N. L. *J. Am. Chem. Soc.* 2009, 132, 38.

(33) Iremonger, S. S.; Liang, J.; Vaidhyanathan, R.; Martens, I.; Shimizu, G. K. H.; Daff, T. D.; Aghaji, M. Z.; Yeganegi, S.; Woo, T. K. *J. Am. Chem. Soc.* 2011, 133, 20048.

(34) Mason, J. A.; Sumida, K.; Herm, Z. R.; Krishna, R.; Long, J. R. *Energy Environ. Sci.* 2011, 4, 3030

(35) Belof, J. L.; Stern, A. C.; Eddaoudi, M.; Space, B. *J. Am. Chem. Soc.* 2007, 129, 15202.

(36) Forrest, K. A.; Pham, T.; McLaughlin, K.; Belof, J. L.; Stern, A. C.; Zaworotko, M. J.; Space, B. *J. Phys. Chem. C.* 2012, 116, 15538.

Information for Example 1:
Experimental Procedures:
Materials and Methods:

All reagents and solvents were purchased in high purity grade and used as received. Powder x-ray diffraction (PXRD) data were recorded on a BrukerD8 Advance X-ray diffractometer at 20 kV, 5 mA for Cuk$\alpha$ ($\lambda$=1.5418 Å), with a scan speed of 0.5 s/step (6°/min) and a step size of 0.05° in 2$\theta$ at room temperature. The calculated XPD patterns were generated using Powder Cell for Windows Version 2.4 (programmed by W. Kraus and G. Nolze, BAM Berlin, 2000). Infrared spectra were recorded on a Nicolet Avatar 320 FT-IR spectrometer. Low pressure gas adsorption isotherms were measured on the Micrometrics ASAP 2020 Surface Area and Porosity Analyzer.

Synthesis:

[Co(bpe)$_2$MoO$_4$], MOOFOUR-1-Co (1)

3 mL of acetonitrile and water (v/v=1:2) was carefully layered over an aqueous solution (3 mL) of CoCl$_2$.6H$_2$O (19.0 mg, 0.08 mmol) and Na$_2$MoO$_4$.2H$_2$O (19.4 mg, 0.08 mmol) in a long thin test tube. 1,2-bis(4-pyridyl)ethene (bpe) (18.2 mg, 0.1 mmol) in 3 mL of acetonitrile and water (v/v=2:1) was slowly layered over the buffer layer. The tube was sealed and left undisturbed at room temperature. After 3 days red block-shaped crystals were isolated from the buffer layer.

[Ni(bpe)$_2$MoO$_4$], MOOFOUR-1-Ni (2)

Crystals of 2 were prepared in the same way as 1 except that NiCl$_2$ (10.4 mg, 0.08 mmol) was used instead of CoCl$_2$.6H$_2$O. After 3 days, the light green block-shaped crystals were harvested.

[Co(bpe)$_2$CrO$_4$], CROFOUR-1-Co (3)

Crystals of 3 were prepared in the same way as 1 except that K$_2$Cr$_2$O$_7$ (23.5 mg, 0.08 mmol) was used instead of Na$_2$MoO$_4$.2H$_2$O. After 3 days red block-shaped crystals were isolated from the buffer layer.

[Ni(bpe)$_2$CrO$_4$], CROFOUR-1-Ni (4)

Crystals of 4 were prepared in the same way as 1 except that NiCl$_2$ (10.4 mg, 0.08 mmol) was used instead of CoCl$_2$.6H$_2$O and K$_2$Cr$_2$O$_7$ (23.5 mg, 0.08 mmol) was used instead of Na$_2$MoO$_4$.2H$_2$O. After 3 days, the green block-shaped crystals were harvested.

Sample Activation for Gas Sorption:

The as-synthesized crystals of MOOFOUR-1-Ni were exchanged with acetonitrile for 72 h (2 times/day) then immersed in methanol for 1 h. The resulting solid was filtered, evacuated at ambient temperature for 36 h and then at 60° C. for 6 h under dynamic pressure. CROFOUR-1-Ni was activated in the same manner except there was no evacuation at 60° C.

FIG. 1.7 illustrates an infrared spectroscopy (diffuse reflectance) for CROFOUR-1-Co, CROFOUR-1-Ni, MOOFOUR-1-Co and MOOFOUR-1-Ni. FIG. 1.8 illustrates experimental and calculated powder X-ray diffraction (PXRD) patterns for MOOFOUR-1-Co. FIG. 1.9 illustrates experimental and calculated powder X-ray diffraction patterns of CROFOUR-1-Co. FIG. 1.10 illustrates pre-activation and post-activation experimental and calculated powder X-ray diffraction patterns for MOOFOUR-1-Ni. FIG. 1.11 illustrates pre-activation and post-activation experimental and calculated powder X-ray diffraction patterns for CROFOUR-1-Ni. FIG. 1.12 illustrates PXRD patterns for MOOFOUR-1-Ni addressing its water and air stability. FIG. 1.13 illustrates CO$_2$ isotherms of MOOFOUR-1-Ni and CROFOUR-1-Ni measured at 195 K. FIG. 1.14 illustrates CO$_2$ adsorption isotherms of MOOFOUR-1-Ni and CROFOUR-1-Ni measured at 273 K and 283 K.

Calculation of Isosteric Heat of Adsorption ($Q_{st}$):

The $Q_{st}$ values for MOOFOUR-1-Ni and CROFOUR-1-Ni have been calculated according to virial equation using the fitted adsorption isotherms at 273 K and 298 K correspondingly it has been calculated using the fitting of the adsorption isotherms at three different temperatures, 273 K, 283 K and 298 K.

FIG. 1.15 illustrates CO$_2$ adsorption isotherms of MOOFOUR-1-Ni at 273 K and 298 K fitted using the virial equation. FIG. 1.16 illustrates CO$_2$ adsorption isotherms of MOOFOUR-1-Ni at 273 K, 283 K and 298 K fitted using the virial equation. FIG. 1.17 illustrates CO$_2$ isosteric heats of adsorption ($Q_{st}$) of MOOFOUR-1-Ni using the fitted data measured at two (273 K and 298 K) and three (273 K, 283 K and 273 K) temperatures. FIG. 1.18 illustrates $CO_2$ adsorption isotherms of CROFOUR-1-Ni fitted using the virial equation. FIG. 1.19 illustrates $CO_2$ adsorption isotherms of CROFOUR-1-Ni at 273 K, 283 K and 298 K fitted using the virial equation. FIG. 1.20 illustrates $CO_2$ isosteric heats of adsorption ($Q_{st}$) of CROFOUR-1-Ni using the fitted data measured at two (273 K and 298 K) and three (273 K, 283 K and 273 K) temperatures.

Ideal Adsorbed Solution Theory:

Ideal adsorbed solution theory, developed by Myers and Prausnitz,[1] was used to estimate the selectivities of $CO_2/N_2$ (10:90) and $CO_2/CH_4$ (50:50) mixture compositions in CROFOUR-1-Ni and MOOFOUR-1-Ni from their respective single-component isotherms. The isotherms were fitted to the dual-site Langmuir-Freundlich equation:[2]

$$n = \frac{n_{m1} b_1 P^{\left(\frac{1}{t_1}\right)}}{1 + b_1 P^{\left(\frac{1}{t_1}\right)}} + \frac{n_{m2} b_2 P^{\left(\frac{1}{t_2}\right)}}{1 + b_2 P^{\left(\frac{1}{t_2}\right)}}$$

Here, n is the amount adsorbed per mass of adsorbent (in mol/kg), P is the total pressure (in kPa) of the bulk gas at equilibrium with the adsorbed phase, $n_{m1}$ and $n_{m2}$ are the saturation uptakes (in mol/kg) for sites 1 and 2, $b_1$ and $b_2$ are the affinity coefficients (in $kPa^{-1}$) for sites 1 and 2, and $t_1$ and $t_2$ represent the deviations from the ideal homogeneous surface for sites 1 and 2. All isotherms were fitted with $R^2 > 0.9999$.

The fitted parameters were then used to predict multi-component adsorption. The mole fraction of each species in the adsorbed phase can be calculated by solving the expression:

$$\int_0^{\frac{Py_i}{x_i}} \frac{n_i(P)}{P} dP = \int_0^{\frac{Py_j}{x_j}} \frac{n_j(P)}{P} dP$$

where $x_i$ and $y_i$ are the adsorbed and bulk phase mole fractions of component i, respectively. In order to solve for $x_i$, two quantities must be specified, specifically P and $y_i$. The quantity $x_i$ was determined using numerical analysis and root exploration. The selectivity for component i relative to component j can be calculated via the following:

$$S_{i/j} = \frac{x_i}{x_j} \frac{y_j}{y_i}$$

FIG. 1.21 illustrates IAST calculated selectivity for a 50:50 $CO_2:CH_4$ mixture based upon the experimentally observed adsorption isotherms of the pure gases for MOOFOUR-1-Ni and CROFOUR-1-Ni. FIG. 1.22 illustrates IAST calculated selectivity for a 10:90 $CO_2: N_2$ mixture based upon experimentally observed adsorption isotherms of the pure gases for MOOFOUR-1-Ni and CROFOUR-1-Ni. FIGS. 1.23A-E illustrates adsorbed $CO_2$ molecules in MOOFOUR-1-Ni showing: 1.23A Side view of the primary binding site (site I). 1.23B Top view of the primary binding site (site I). 1.23C Side view of the secondary binding site (site II). 1.23D Top view of the secondary binding site (site II). 1.23E Side view of the both binding sites (site I and II). FIG. 1.23 illustrates snapshot of a 1×1×2 unit cell of CROFOUR-1-Ni during the simulation showing the strong interaction between $CO_2$ molecules and 3 pairs of terminal oxygen atoms sticking out from the chromate ion (see box).

Single-Crystal X-Ray Diffraction:

The X-ray diffraction data for MOOFOUR-1-Ni were collected using synchrotron radiation, λ=0.41328 Å, at the Advanced Photon Source, Chicago Ill. The X-ray diffraction data for MOOFOUR-1-Co, CROFOUR-1-Ni and CROFOUR-1-Co were collected using Bruker-AXS SMART-APEXIICCD diffractometer using CuKα (λ=1.54178 Å). Indexing was performed using APEX2[3] (Difference Vectors method). Data integration and reduction were performed using SaintPlus 6.01.[4] Absorption correction was performed by multi-scan method implemented in SADABS.[5] Space groups were determined using XPREP implemented in APEX2.[3] The structure was solved using SHELXS-97 (direct methods) and refined using SHELXL-97 (full-matrix least-squares on $F^2$) contained in APEX2[3] and WinGXv1.70.01[6]-9 programs packages. Hydrogen atoms were placed in geometrically calculated positions and included in the refinement process using riding model with isotropic thermal parameters: Uiso(H)=1.2 Ueq(—CH). Acetonitrile molecules were located in the cavities of MOOFOUR-1-Ni, MOOFOUR-1-Co and CROFOUR-1-Ni. The remaining disordered solvent was refined as oxygen atoms ($H_2O$). For CROFOUR-1-Co the contribution of heavily disordered solvent molecules was treated as diffuse using the Squeeze procedure implemented in Platon.[10,11] Crystals of MOOFOUR-1-Ni, MOOFOUR-1-Co and CROFOUR-1-Co were racemically twinned (R32 space group).

References for Supplemental Information:

[1] Myers, A. L.; Prausnitz, J. M. *AIChE Journal* 1965, 11, 121-127.

[2] Yang, R. T. *Gas Separation by Adsorption Processes*; Imperial College Press, 1986.

[3] Bruker (2010). APEX2). BrukerAXS Inc., Madison, Wis., USA.

TABLE 1

The fitted parameters for the dual-site Langmuir-Freundlich equation for the single-component isotherms of $CO_2$, $N_2$, and $CH_4$ in CROFOUR-1-Ni and MOOFOUR-1-Ni at 298 K.

|  | CROFOUR-1-Ni | | | MOOFOUR-1-Ni | | |
|---|---|---|---|---|---|---|
|  | $CO_2$ | $N_2$ | $CH_4$ | $CO_2$ | $N_2$ | $CH_4$ |
| $n_{m1}$ (mol/kg) | 4.914843 | 0.215713 | 1.919022 | 6.556938 | 22.209305 | 5.702940 |
| $n_{m2}$ (mol/kg) | 3.047214 | 5.647549 | 1.248420 | 3.032790E-02 | 5.781674E-02 | 0.720602 |
| $b_1$ ($kPa^{-1}$) | 1.363105E-04 | 8.017059E-07 | 4.494827E-07 | 7.204357E-02 | 4.462305E-06 | 1.544469E-03 |
| $b_2$ ($kPa^{-1}$) | 0.200857 | 7.241491E-04 | 6.269775E-03 | 3.434810E-02 | 2.211130E-02 | 3.600762E-03 |
| $t_1$ | 0.762931 | 0.368983 | 0.404170 | 2.199954 | 0.640078 | 1.322732 |
| $t_2$ | 1.822999 | 1.180533 | 0.905631 | 0.181479 | 0.706056 | 0.8060724 |

[4] Bruker (2009). SAINT.Data Reduction Software.BrukerAXS Inc., Madison, Wis., USA.
[5] Sheldrick, G. M. (2008). *SADABS. Program for Empirical Absorption Correction*. University of Gottingen, Germany.
[6] FarrugiaL. J. Appl. Cryst. (1999). 32, 837±838
[7] Sheldrick, G. M. (1997) SHELXL-97. Program for the Refinement of Crystal
[8] Sheldrick, G. M. (1990) ActaCryst. A46, 467-473
[9] Sheldrick, G. M. (2008) ActaCryst. A64, 112-122.
[10] Spek, T. L., Acta Cryst. (1990) A46, 194-201.
[11] Spek, T. L., Acta Cryst. (1990) A46, c34.
[12] F. H. Allen, ActaCryst., (2002) B58, 380-388

Example 2

Synthesis, Characterization and Gas Sorption Properties of [Ni(Bpe)$_2$(WO$_4$)](WOFOUR-1-Ni)

An aqueous solution (4 mL) of NiCl$_2$.6H$_2$O (Sigma-Aldrich Inc., 98%, 11.9 mg, 0.05 mmol) was mixed with an aqueous solution (4 mL) of Na$_2$WO$_4$.2H$_2$O (Sigma-Aldrich Inc., 99%, 16.5 mg, 0.05 mmol) in a long thin test tube, the resulting turbid solution was carefully layered under 1,2-bis(4-pyridyl)ethene (bpe) (Sigma-Aldrich Inc., 97%, 18.2 mg, 0.1 mmol) in 4 mL of acetonitrile and water (v/v=2:1). The tube was sealed and left undisturbed at room temperature. After one week light green block-shaped crystals were isolated (yield: 9 mg, 24% based on NiCl$_2$.6H$_2$O).

FIG. 2.1 illustrates a self-catenated square grid connected with the angular WO$_4^{-2}$ pillars to afford 6-c uninodal mmo topology net of WOFOUR-1-Ni.

FIG. 2.2 illustrates the single crystal x-ray structure of WOFOUR-1-Ni viewed along [001] (left). View of the cavity in WOFOUR-1-Ni along [001] (right). H atoms omitted for clarity.

FIG. 2.3 illustrates reversible single component gas adsorption isotherms of WOFOUR-1-Ni.

Example 3

Synthesis and Characterization of [Co(bpe)$_2$(WO$_4$)] (WOFOUR-1-Co)

An aqueous solution (4 mL) of CoCl$_2$.6H$_2$O (Sigma-Aldrich Inc., 98%, 11.9 mg, 0.05 mmol) was mixed with an aqueous solution (4 mL) of Na$_2$WO$_4$.2H$_2$O (Sigma-Aldrich Inc., 99%, 16.5 mg, 0.05 mmol) in a long thin test tube, the resulting turbid solution was carefully layered under 1,2-bis(4-pyridyl)ethene (bpe) (Sigma-Aldrich Inc., 97%, 18.2 mg, 0.1 mmol) in 4 mL of acetonitrile and water (v/v=2:1). The tube was sealed and left undisturbed at room temperature. After one week red block-shaped crystals were isolated (yield: 10 mg, 27% based on CoCl$_2$.6H$_2$O).

FIG. 3.1 illustrates the single crystal x-ray structure of WOFOUR-1-Co viewed along [001].

Example 4

Synthesis and Characterization of [Ni(bpa)$_2$(MoO$_4$)] (MOOFOUR-2-Ni)

2 mL of acetonitrile and water (v/v=1:2) was carefully layered over an aqueous solution (4 mL) of NiCl$_2$.6H$_2$O (Sigma-Aldrich Inc., 98%, 38.1 mg, 0.16 mmol) and Na$_2$MoO$_4$.2H$_2$O (Sigma-Aldrich Inc., 98%, 38.8 mg, 0.16 mmol) in a long thin test tube. 1,2-bis(4-pyridyl)ethane (bpa) (Sigma-Aldrich Inc., 99%, 36.8 mg, 0.2 mmol) in 4 mL of acetonitrile and water (v/v=2:1) was slowly layered over the buffer layer. The tube was sealed and left undisturbed at room temperature. After 2 days light blue block-shaped crystals were isolated from the buffer layer (yield: 16 mg, 15.1% based on NiCl$_2$.6H$_2$O).

FIG. 4.1 illustrates the single crystal x-ray structure of MOOFOUR-2-Ni viewed along [001].

Example 5

Synthesis, Characterization and Gas Sorption Properties of [Ni(Bpa)$_2$(CrO$_4$)](CROFOUR-2-Ni)

2 mL of acetonitrile and water (v/v=1:2) was carefully layered over an aqueous solution (4 mL) of NiCl$_2$.6H$_2$O (Sigma-Aldrich Inc., 98%, 38.1 mg, 0.16 mmol) and K$_2$CrO$_4$ (Sigma-Aldrich Inc., 99%, 31.0 mg, 0.16 mmol) in a long thin test tube. 1,2-bis(4-pyridyl)ethane (bpa) (Sigma-Aldrich Inc., 99%, 36.8 mg, 0.2 mmol) in 4 mL of acetonitrile and water (v/v=2:1) was slowly layered over the buffer layer. The tube was sealed and left undisturbed at room temperature. After 2 days green block-shaped crystals were isolated from the buffer layer (yield: 15 mg, 15.1% based on NiCl$_2$.6H$_2$O).

FIG. 5.1 illustrates the single crystal x-ray structure of CROFOUR-2-Ni viewed along [001].

FIG. 5.2 illustrates a view of the two cavities in CROFOUR-2-Ni along [001].

FIG. 5.3 illustrates reversible single component gas adsorption isotherms of CROFOUR-2-Ni.

Example 6

Synthesis and Characterization of [Ni(bpa)$_2$(WO$_4$)] (WOFOUR-2-Ni)

An aqueous solution (4 mL) of NiCl$_2$.6H$_2$O (Sigma-Aldrich Inc., 98%, 11.9 mg, 0.05 mmol) was mixed with an aqueous solution (4 mL) of Na$_2$WO$_4$.2H$_2$O (Sigma-Aldrich Inc., 99%, 16.5 mg, 0.05 mmol) in a long thin test tube, the resulting turbid solution was carefully layered under 1,2-bis(4-pyridyl)ethane (bpa) (Sigma-Aldrich Inc., 99%, 18.4 mg, 0.1 mmol) in 4 mL of acetonitrile and water (v/v=2:1). The tube was sealed and left undisturbed at room temperature. After 3 days light blue block-shaped crystals were isolated (yield: 12 mg, 32% based on NiCl$_2$.6H$_2$O).

FIG. 6.1 illustrates the single crystal x-ray structure of WOFOUR-2-Ni viewed along [001].

Example 7

Synthesis and Characterization of [Co(bpa)$_2$(WO$_4$)] (WOFOUR-2-Co)

An aqueous solution (4 mL) of CoCl$_2$.6H$_2$O (Sigma-Aldrich Inc., 98%, 11.9 mg, 0.05 mmol) was mixed with an aqueous solution (4 mL) of Na$_2$WO$_4$.2H$_2$O (Sigma-Aldrich Inc., 99%, 16.5 mg, 0.05 mmol) in a long thin test tube, the resulting turbid solution was carefully layered under 1,2-bis(4-pyridyl)ethane (bpa) (Sigma-Aldrich Inc., 99%, 18.4 mg, 0.1 mmol) in 4 mL of acetonitrile and water (v/v=2:1). The tube was sealed and left undisturbed at room temperature. After 3 days red block-shaped crystals were isolated (yield: 10 mg, 26% based on CoCl$_2$.6H$_2$O).

FIG. 7.1 illustrates the single crystal x-ray structure of WOFOUR-2-Co viewed along [001].

Example 8

Synthesis, Characterization and Gas Sorption Properties of [Ni(zbp)$_2$(CrO$_4$)](CROFOUR-3-Ni)

2 mL of acetonitrile and water (v/v=1:2) was carefully layered over an aqueous solution (4 mL water and one drop acetonitrile) of NiCl$_2$.6H$_2$O (Sigma-Aldrich Inc., 98%, 38.1 mg, 0.16 mmol) and K$_2$CrO$_4$ (Sigma-Aldrich Inc., 99%, 31.0 mg, 0.16 mmol) in a long thin test tube. 4,4'-azopyridine (zbp) (Sigma-Aldrich Inc., 99%, 36.8 mg, 0.2 mmol) in 4 mL of acetonitrile and water (v/v=2:1) was slowly layered over the buffer layer. The tube was sealed and left undisturbed at room temperature. After one week dark red block-shaped crystals were isolated from the buffer layer (yield: 13 mg, 15% based on NiCl$_2$.6H$_2$O).

FIG. 8.1 illustrates the single crystal x-ray structure of CROFOUR-3-Ni viewed along [001], H atoms omitted for clarity.

FIG. 8.2 illustrates a view of the two cavities in CROFOUR-3-Ni along [001].

FIG. 8.3 illustrates reversible single component gas adsorption isotherms of CROFOUR-3-Ni.

Example 9

Synthesis and Characterization of [Ni(zbp)$_2$(MoO$_4$)] (MOOFOUR-3-Ni)

2 mL of acetonitrile and water (v/v=1:2) was carefully layered over an aqueous solution (4 mL water and one drop acetonitrile) of NiCl$_2$.6H$_2$O (Sigma-Aldrich Inc., 98%, 38.1 mg, 0.16 mmol) and Na$_2$MoO$_4$.2H$_2$O (Sigma-Aldrich Inc., 98%, 38.8 mg, 0.16 mmol) in a long thin test tube. 4,4'-azopyridine (zbp) (Sigma-Aldrich Inc., 99%, 36.8 mg, 0.2 mmol) in 4 mL of acetonitrile and water (v/v=2:1) was slowly layered over the buffer layer. The tube was sealed and left undisturbed at room temperature. After one week dark red block-shaped crystals were isolated from the buffer layer (yield: 5 mg, 9% based on NiCl$_2$.6H$_2$O).

FIG. 9.1 illustrates the single crystal x-ray structure of MOOFOUR-3-Ni viewed along [001], H atoms omitted for clarity.

Example 10

Synthesis and Characterization of [Ni(bpb)$_2$(CrO$_4$)] (CROFOUR-4-Ni)

1 mL of acetonitrile and water (v/v=1:2) was carefully layered over an aqueous solution (4 mL water and one drop acetonitrile) of NiCl$_2$.6H$_2$O (Sigma-Aldrich Inc., 98%, 23.8 mg, 0.1 mmol) and K$_2$CrO$_4$ (Sigma-Aldrich Inc., 99%, 19.4 mg, 0.1 mmol) in a long thin test tube. 1,4-bis(4-pyridyl)benzene (bpb) (has been synthesized according to the previously reported procedure[1], 23.2 mg, 0.1 mmol) in 4 mL of acetonitrile and water (v/v=2:1) was slowly layered over the buffer layer.

The tube was sealed and left undisturbed at room temperature. After one week yellowish green crystals were isolated from the buffer layer (yield: 3 mg, 5% based on NiCl$_2$.6H$_2$O).

1—Y.-F. Han, Y.-J. Lin, W.-G. Jia and G.-X. Jin, *Organometallics*, 2008, 27, 4088-4097.

FIG. 10.1 illustrates the single crystal x-ray structure of CROFOUR-4-Ni viewed along [001], H atoms omitted for clarity.

Example 11

Synthesis and Characterization of [Ni(bpb)$_2$(MoO$_4$)] (MOOFOUR-4-Ni)

2 mL of acetonitrile and water (v/v=1:2) was carefully layered over an aqueous solution (4 mL water and one drop acetonitrile) of NiCl$_2$.6H$_2$O (Sigma-Aldrich Inc., 98%, 23.8 mg, 0.1 mmol) and Na$_2$MoO$_4$.2H$_2$O (Sigma-Aldrich Inc., 98%, 24.3 mg, 0.16 mmol) in a long thin test tube. 1,4-bis(4-pyridyl)benzene (bpb) (has been synthesized according to the previously reported procedure[1], 23.2 mg, 0.1 mmol) in 4 mL of acetonitrile and water (v/v=2:1) was slowly layered over the buffer layer. The tube was sealed and left undisturbed at room temperature. After one week light green crystals were isolated from the buffer layer (yield: 13 mg, 16% based on NiCl$_2$.6H$_2$O).

1—Y.-F. Han, Y.-J. Lin, W.-G. Jia and G.-X. Jin, *Organometallics*, 2008, 27, 4088-4097.

FIG. 11.1 illustrates the single crystal x-ray structure of MOOFOUR-4-Ni viewed along [001] (left). View of the cavity in MOOFOUR-4-Ni along [001] (right). H atoms omitted for clarity.

Example 12

An mmo net is a versatile metal organic material (MOM) platform of general formula [M(L)$_2$(P)]$_n$ (M=transition metal, main group metal, lanthanide, actinide; L=dipyridyl-type linker or related N-donor linker; M'O$_4$=angular inorganic oxyanion pillar) (See FIG. 12.1). They can be described as self-catenated neutral nets built from [M(L)$_2$] square grids linked by angular pillars such as CrO$_4^{-2}$, MoO$_4^{-2}$ or WO$_4^{-2}$. They are the first examples of 6-connected $4^8.6^7$ topology nets, have been assigned RCSR code mmo after their discoverer, Mona Mohamed, and were first reported in 2012.[1]

mmo nets are prepared by a facile 1-step self-assembly reaction that is conducted at room temperature.

mmo nets are of interest because they are inexpensive and particularly facile to synthesize. In addition, their modular nature means they can be fine-tuned at 3 sites (M, linker and M') without changing the overall structure. This allows for systematic study of structure-property relationships. Furthermore, the prototypal mmo nets are extraordinary stable as they retain their crystallinity in water over a wide range of pH and they are stable in air and boiling water for months. Also, they represent the first examples of porous MOMs based on CrO$_4^{-2}$, MoO$_4^{-2}$ or WO$_4^{-2}$ moieties.[1-3] Lastly, the protypal mmo nets, MOFOUR-1-Ni, CROFOUR-1-Ni and WOFOUR-1-Ni, are CO$_2$ adsorbents that outperform many other MOMs, even those with unsaturated metal centers, UMCs, or amine functionalized MOMs. This performance has been ascribed to strong quadrupole-quadrupole interactions between CO$_2$ and the metal oxide binding sites that line the pore walls.

References, each of which is incorporated herein by reference:

1. Mohamed, M. H.; Elsaidi, S. K.; Wojtas, L.; Pham, T.; Forrest, K. A.; Tudor, B.; Space, B.; Zaworotko, M. J. "Highly Selective CO$_2$ Uptake in Uninodal 6-Connected "mmo" Nets Based upon $MO_4^{2-}$ (M=Cr, Mo) Pillars." *Journal of the American Chemical Society* 2012, 134, 19556, DOI:
2. Mohamed, M. H.; Elsaidi, S. K.; Pham, T.; Forrest, K. A.; Tudor, B.; Wojtas, L.; Space, B.; Zaworotko, M. J. "Pillar substitution modulates $CO_2$ affinity in "mmo" topology networks." *Chemical Communications* 2013, 49, 9809, DOI:
3. Burd, S. D.; Nugent, P. S.; Mohamed, M. H.; Elsaidi, S. K.; Zaworotko, M. J. "Square Grid and Pillared Square Grid Coordination Polymers: Fertile Ground for Crystal Engineering of Structure and Function." *CHIMIA International Journal for Chemistry* 2013, 67, 372, DOI:

Example 13

Exemplary mmo nets; MOOFOUR-1-Ni, CROFOUR-1-Ni and WOFOUR-1-Ni, offer exceptional stability in water over a wide range of PH. These MOMs retain crystallinity even when immersed in water for months, boiling water for one day, 0.1 M NaOH for a week, or 0.01 M HCl for one day (See FIGS. 13.1 to 13.3).

In regard to the discussion herein including the Examples above and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the units of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:
1. A metal-organic material (MOM), comprising:
$[M(L)_2P]_n$, wherein $[M(L)_2P]_n$ has a 6-connected $4^8.6^7$ topology net, wherein M is selected from the group consisting of: $Cu^{2+}$, $Zn^{2+}$, $Co^{2+}$, $Ni^{2+}$, $Mn^{2+}$, $Zr^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+3}$, $Cr^{3+}$, $Ru^{3+}$ and $Co^{3+}$, wherein L is a bifunctional N donor group that serves as a linker, and P is an oxyanion with angular geometry, and wherein n is 1 to $10^{18}$.

2. The MOM of claim 1, wherein L is selected from the group consisting of: a dipyridyl-based linker, a pyrazolate-based linker, an imidazolate-based linker, tetrazolate-based linker and a triazolate-based linker.

3. The MOM of claim 1, wherein P is selected from the group consisting of: $CrO_4^{2-}$, $MoO_4^{2-}$, $WO_4^{2-}$, $SO_4^{2-}$, $TiO_4^{2-}$, $SeO_4^{2-}$, $CO_3^{2-}$, $SO_3^{2-}$, $SiO_3^{2-}$, $ZrO_3^{2-}$, $Cr_2O_7^{2-}$, $Mo_2O_7^{2-}$, $S_2O_3^{2-}$, $S_2O_6^{2}$, $S_2O_8^{2-}$, $Ti_3O_7^{2-}$, $PO_4^{2-}$, $VO_4^{2-}$, $AsO_4^{2-}$, $PO_3^{3-}$, $BO_3^{3-}$, and $AsO_3^{3-}$.

4. The MOM of claim 1, wherein $[M(L)_2P]_n$ is represented by $[M(L)_2(M'O_4)]_n$, wherein $[M(g)_2(M'O_4)]_n$ wherein M' is selected from the group consisting of: $Cu^{2+}$, $Zn^{2+}$, $Co^{2+}$, $Ni^{2+}$, $Mn^{2+}$, $Zr^{2+}$, $Fe^{2+}$, $Ca^{2+}$, $Ba^{2+}$, $Cs^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+3}$, $Cr^{3+}$, $Ru^{3+}$, and $Co^{3+}$, and wherein L is selected from the group consisting of: (1) pyrazine, (2) 4,4'-bipyridine, (3) 4,4'-azo-bis(pyridine), (4) 1,2-bis(4-pyridyl)ethene, (5) 1,2-bis(4-pyridyl)ethane, (6) 1,2-di(pyridine-4-yl)ethane-1,2-diol, (7) 3-[(trimethylsilyl)ethynyl]-4-[2-(4-pyridinyl)ethenyl]pyridine, (8) 1,2-bis(4-pyridyl)ethyne, (9) 1,4-bis(4-pyridyl)benzene, (10) 3,6-di(pyridin-4-yl)-1,2,4,5-tetrazine, (11) 4-(9-(pyridin-4-yl)anthracen-10-yl)pyridine, (12) 4,4'-bis(4-pyridyl)biphenyl, (13) N,N'-bis(4-pyridyl)pyromellitic diimide, (14) N,N'-di(pyridyl)-1,4,5,8-naphthalenetetracarboxydiimide, (15) 4,4'-bipyrazolyl, (16) 1,4-bis(1H-pyrazol-4-yl)benzene, (17) 4,4'-buta-1,3-diyne-1,4-diylbis(1H-pyrazole), (18) N,N'-bis(1H-pyrazol-4-yl)pyromellitic diimide, (19) N,N'-bis(1H-pyrazol-4-yl)-1,4,5,8-naphthalenetetracarboxydiimide, (20) 4,4'-bis(1H-pyrazol-4-yl)biphenyl, (21) N,N'-bis(1H-pyrazol-4-yl)-1,4-benzenedicarboxamide, (22) 4,4'-benzene-1,4-diylbis(1H-pyrazole), (23) Imidazole, (24) 2-methylimidazole, (25) 2-ethylimidazole, (26) 2-nitroimidazole, (27) benzimidazole, (28) purine, (29) 1,4-bis(1-imidazolyl)benzene, (30) 9,10-(1-imidazolyl)anthracene, (30) 4,4'-bis(1-imidazolyl)biphenyl, (32) tetrakis(1-Imidazolyl)borate, (33) 1,2,4-triazol, (34) 4,4'-bis-1,2,4-triazol, (35) 4,4'-azo-1,2,4-triazol, (36) 1,3-bis(1,2,4-triazol-1-yl)-propane, (37) 1,4-bis(1,2,4-triazol-1-yl)-butane, (38) 1,4-bis(1,2,4-triazol-1-ylmethyl)-benzene, and (39) 4,4'-bis(1,2,4-triazol-1-ylmethyl)-1,1'-biphenyl.

5. The MOM of claim 1, comprising:
$[M(L)_2P]_n$, wherein $[M(L)_2P]_n$ has a 6-connected $4^8.6^7$ topology net, wherein M is Co or Ni, wherein L is a bifunctional N donor group that serves as a linker, and P is an oxyanion with angular geometry, and wherein n is 1 to $10^{18}$,
wherein $[M(L)_2P]_n$ is represented by $[M(L)_2(M'O_4)]_n$, wherein $[M(g)_2(M'O_4)]_n$ wherein M' is Mo, W, or Cr, and
wherein L is selected from the group consisting of: (1) pyrazine, (2) 4,4'-bipyridine, (3) 4,4'-azo-bis(pyridine), (4) 1,2-bis(4-pyridyl)ethene, (5) 1,2-bis(4-pyridyl)ethane, (6) 1,2-di(pyridine-4-yl)ethane-1,2-diol, (7) 3-[(trimethylsilyl)ethynyl]-4-[2-(4-pyridinyl)ethenyl]pyridine, (8) 1,2-bis(4-pyridyl)ethyne, (9) 1,4-bis(4-pyridyl)benzene, (10) 3,6-di(pyridin-4-yl)-1,2,4,5-tetrazine, (11) 4-(9-(pyridin-4-yl)anthracen-10-yl)pyridine, (12) 4,4'-bis(4-pyridyl)biphenyl, (13) N,N'-bis(4-pyridyl)pyromellitic diimide, (14) N,N'-di(pyridyl)-1,4,5,8-naphthalenetetracarboxydiimide, (15) 4,4'-bipyrazolyl, (16) 1,4-bis(1H-pyrazol-4-yl)benzene, (17) 4,4'-buta-1,3-diyne-1,4-diylbis(1H-pyrazole), (18) N,N'-bis(1H-pyrazol-4-yl)pyromellitic diimide, (19) N,N'-bis(1H-pyrazol-4-yl)-1,4,5,8-naphthalenetetracarboxydiimide, (20) 4,4'-bis(1H-pyrazol-4-yl)biphenyl, (21) N,N'-bis(1H-pyrazol-4-yl)-1,4-benzenedicarboxamide, (22) 4,4'-benzene-1,4-diylbis(1H-pyrazole), (23) Imidazole, (24) 2-methylimidazole, (25) 2-ethylimidazole, (26) 2-nitroimidazole, (27) benzimidazole, (28) purine, (29) 1,4-bis(1-imidazolyl)benzene, (30) 9,10-(1-imidazolyl)anthracene, (30) 4,4'-bis(1-imidazolyl)biphenyl, (32) tetrakis(1-Imidazolyl)borate, (33) 1,2,4-triazol, (34) 4,4'-bis-1,2,4-triazol, (35) 4,4'-azo- 1,2,4-triazol, (36) 1,3-bis(1,2,4-triazol-1-yl)-propane, (37) 1,4-bis(1,2,4-triazol-1-yl)-butane, (38) 1,4-bis(1,2,4-triazol-1-ylmethyl)-benzene, and (39) 4,4'-bis(1,2,4-triazol-1-ylmethyl)-1,1'-biphenyl.

6. The MOM of claim 1, comprising:

[M(L)$_2$P]$_n$, wherein [M(L)$_2$P]$_n$ has a 6-connected $4^8.6^7$ topology net, wherein M is Co or Ni, wherein L is a bifunctional N donor group that serves as a linker, and P is an oxyanion with angular geometry, and wherein n is 1 to $10^{18}$, wherein [M(L)$_2$P]$_n$ is represented by [M(L)$_2$(M'O$_4$)]$_n$, wherein [M(q)$_2$(M'O$_4$)]$_n$ wherein M' is Mo, W, or Cr, and wherein L is selected from the group consisting of: (1) pyrazine, (2) 4,4'-bipyridine, (3) 4,4'-azo-bis(pyridine), (4) 1,2-bis(4-pyridyl)ethene, (5) 1,2-bis(4-pyridyl)ethane, (6) 1,2-di(pyridine-4-yl)ethane-1,2-diol, (7) 3-[(trimethylsilyl)ethynyl]-4-[2-(4-pyridinyl)ethenyl]pyridine, (8) 1,2-bis(4-pyridyl)ethyne, (9) 1,4-bis(4-pyridyl)benzene, (10) 3,6-di(pyridin-4-yl)-1,2,4,5-tetrazine, (11) 4-(9-(pyridin-4-yl)anthracen-10-yl)pyridine, (12) 4,4'-bis(4-pyridyl)biphenyl, (13) N,N'-bis(4-pyridyl)pyromellitic diimide, (14) N,N'-di(pyridyl)-1,4,5,8-naphthalenetetracarboxydiimide, (15) 4,4'-bipyrazolyl, (16) 1,4-bis(1H-pyrazol-4-yl)benzene, (17) 4,4'-buta-1,3-diyne-1,4-diylbis(1H-pyrazole), (18) N,N'-bis(1H-pyrazol-4-yl)pyromellitic diimide, (19) N,N'-bis(1H-pyrazol-4-yl)-1,4,5,8-naphthalenetetracarboxydiimide, (20) 4,4'-bis(1H-pyrazol-4-yl)biphenyl, (21) N,N'-bis(1H-pyrazol-4-yl)-1,4-benzenedicarboxamide, (22) 4,4'-benzene-1,4-diylbis(1H-pyrazole), (23) Imidazole, (24) 2-methylimidazole, (25) 2-ethylimidazole, (26) 2-nitroimidazole, (27) benzimidazole, (28) purine, (29) 1,4-bis(1-imidazolyl)benzene, (30) 9,10-(1-imidazolyl)anthracene, (30) 4,4'-bis(1-imidazolyl)biphenyl, (32) tetrakis(1-Imidazolyl)borate, (33) 1,2,4-triazol, (34) 4,4'-bis-1,2,4-triazol, (35) 4,4'-azo-1,2,4-triazol, (36) 1,3-bis(1,2,4-triazol-1-yl)-propane, (37) 1,4-bis(1,2,4-triazol-1-yl)-butane, (38) 1,4-bis(1,2,4-triazol-1-ylmethyl)-benzene, and (39) 4,4'-bis(1,2,4-triazol-1-ylmethyl)-1,1'-biphenyl, and wherein the MOM is selected from the group consisting of: [Co(bpe)$_2$(CrO$_4$)], [Ni(bpe)$_2$(CrO$_4$)]$_n$, [Ni(bpa)$_2$(CrO$_4$)]$_n$, [Ni(zbp)$_2$(CrO$_4$)]$_n$, [Ni(bpb)$_2$(CrO$_4$)]$_n$, [Co(bpe)$_2$(MoO$_4$)]$_n$, [Ni(bpe)$_2$(MoO$_4$)]$_n$, [Ni(bpa)$_2$(MoO$_4$)]$_n$, [Ni(zbp)$_2$(MoO$_4$)]$_n$, [Ni(bpb)$_2$(MoO$_4$)]$_n$, [Co(bpe)$_2$(WO$_4$)]$_n$, [Ni(bpe)$_2$(WO$_4$)]$_n$, [Co(bpa)$_2$(WO$_4$)]$_n$, and [Ni(bpa)$_2$(WO$_4$)]$_n$.

7. The MOM of claim 1, comprising:

[M(L)$_2$P]$_n$, wherein [M(L)$_2$P]$_n$ has a 6-connected $4^8.6^7$ topology net, wherein M is selected from the group consisting of: Cu$^{2+}$, Zn$^{2+}$, Co$^{2+}$, Ni$^{2+}$, Mn$^{2+}$, Zr$^{2+}$, Fe$^{2+}$, Ca$^{2+}$, Ba$^{2+}$, Cs$^{2+}$, Pb$^{2+}$, Pt$^{2+}$, Pd$^{2+}$, Ru$^{2+}$, Rh$^{2+}$, Cd$^{2+}$, Mg$^{+2}$, Al$^{+3}$, Fe$^{+3}$, Cr$^{3+}$, Ru$^{3+}$ and Co$^{3+}$, wherein L is a bifunctional N donor group that serves as a linker, and P is an oxyanion with angular geometry, and wherein n is 1 to $10^{18}$, and wherein L is selected from: 1,2-bis(4-pyridyl)ethene (bpe), 1,2-bis(4-pyridyl)ethane (bpa), 4,4'-azopyridine (zbp), or 1,4-bis(4-pyridyl)benzene (bpb).

8. A method of capturing a polarizable gas in a gas, comprising:

exposing the gas to a [M(L)$_2$P]$_n$, wherein [M(L)$_2$P]$_n$ has a 6-connected $4^8.6^7$ topology net, wherein M is selected from the group consisting of: Cu$^{2+}$, Zn$^{2+}$, Co$^{2+}$, Ni$^{2+}$, Mn$^{2+}$, Zr$^{2+}$, Fe$^{2+}$, Ca$^{2+}$, Ba$^{2+}$, Cs$^{2+}$, Pb$^{2+}$, Pt$^{2+}$, Pd$^{2+}$, Ru$^{2+}$, Rh$^{2+}$, Cd$^{2+}$, Mg$^{+2}$, Al$^{+3}$, Fe$^{+3}$, Cr$^{3+}$, Ru$^{3+}$ and Co$^{3+}$, wherein L is a bifunctional N donor group that serves as a linker, and P is an oxyanion with angular geometry, wherein n is 1 to $10^{18}$; and capturing the polarizable gas in the [M(L)$_2$P]$_n$, wherein the polarizable gas is removed from the gas after the exposure to the MOM to form a modified gas.

9. The method of claim 8, wherein the polarizable gas is CO$_2$, wherein the gas includes at least one of the following gases: N$_2$, H$_2$, and CH$_4$, wherein the [M(L)$_2$P]$_n$ has a greater relative affinity for CO$_2$ over each one of N$_2$, H$_2$, and CH$_4$.

10. A method of separating components in a gas, comprising:

exposing a gas including a first component and a second component to a metal-organic material (MOM), wherein the MOM includes a [M(L)$_2$P]$_n$, wherein [M(L)$_2$P]$_n$ has a 6-connected $4^8.6^7$ topology net, wherein M is selected from the group consisting of: Cu$^{2+}$, Zn$^{2+}$, Co$^{2+}$, Ni$^{2+}$, Mn$^{2+}$, Zr$^{2+}$, Fe$^{2+}$, Ca$^{2+}$, Ba$^{2+}$, Cs$^{2+}$, Pb$^{2+}$, Pt$^{2+}$, Pd$^{2+}$, Ru$^{2+}$, Rh$^{2+}$, Cd$^{2+}$, Mg$^{+2}$, Al$^{+3}$, Fe$^{+3}$, Cr$^{3+}$, Ru$^{3+}$ and Co$^{3+}$, wherein L is a bifunctional N donor group that serves as a linker, and P is an oxyanion with angular geometry, wherein n is 1 to $10^{18}$, wherein the MOM has a greater relative affinity for the first component over a second component; and capturing the first component in the MOM.

11. The method of claim 10, wherein the first component is CO$_2$ and the second component is N$_2$.

12. The method of claim 10, wherein the first component is CO$_2$ and the second component is H$_2$.

13. The method of claim 10, wherein the first component is CO$_2$ and the second component is CH$_4$.

* * * * *